United States Patent [19]

Waknine

[11] Patent Number: 5,444,104

[45] Date of Patent: * Aug. 22, 1995

[54] DENTAL RESIN MATERIALS

[75] Inventor: Samuel Waknine, Branford, Conn.

[73] Assignee: Jeneric/Pentron, Inc., Wallingford, Conn.

[ * ] Notice: The portion of the term of this patent subsequent to Jan. 4, 2011 has been disclaimed.

[21] Appl. No.: 135,303

[22] Filed: Oct. 12, 1993

Related U.S. Application Data

[60] Division of Ser. No. 827,566, Jan. 28, 1992, Pat. No. 5,276,068, which is a continuation of Ser. No. 339,097, Apr. 14, 1989, abandoned, which is a continuation-in-part of Ser. No. 195,351, May 12, 1988, abandoned, which is a continuation of Ser. No. 843,081, Mar. 27, 1986, abandoned, which is a continuation-in-part of Ser. No. 717,332, Mar. 29, 1985, abandoned.

[51] Int. Cl.$^6$ ............................................. C08F 2/50
[52] U.S. Cl. ..................................... 522/24; 522/28; 522/75; 522/79; 522/81; 522/82; 522/83; 522/96; 522/103; 522/908; 433/222.1; 433/228.1; 523/116; 526/313; 526/314; 528/75
[58] Field of Search ............... 522/24, 28, 75, 79, 522/81, 82, 83, 96, 103, 908; 433/222.1, 228.1; 523/116; 526/313, 314; 528/75

[56] References Cited

U.S. PATENT DOCUMENTS

| | | | |
|---|---|---|---|
| 3,200,142 | 8/1965 | Bowen | 523/116 |
| 3,716,571 | 2/1973 | Berlin et al. | 558/267 |
| 3,815,239 | 6/1974 | Lee, Jr. et al. | 423/220 |
| 3,985,793 | 10/1976 | Brooks et al. | 562/426 |
| 4,076,742 | 2/1978 | Berlin et al. | 526/313 |
| 4,107,386 | 8/1978 | Gruber et al. | 428/412 |
| 4,126,737 | 11/1978 | Gruber et al. | 526/270 |
| 4,137,253 | 1/1979 | Piteau et al. | 558/280 |
| 4,246,336 | 1/1981 | Berlin et al. | 430/288 |
| 4,302,381 | 11/1981 | Omura et al. | 523/116 |
| 4,479,782 | 10/1984 | Orlowski et al. | 433/220 |
| 4,581,389 | 4/1986 | Schaefer | 522/9 |
| 4,588,756 | 5/1986 | Bowen | 523/116 |
| 5,276,068 | 1/1994 | Waknine | 522/24 |

FOREIGN PATENT DOCUMENTS

| | | |
|---|---|---|
| 1428454 | 3/1976 | United Kingdom . |
| 732291 | 5/1980 | U.S.S.R. . |
| 1113122 | 9/1984 | U.S.S.R. . |

OTHER PUBLICATIONS

Barkalov, "Postradiation curing of oligo (carbonate acrylates)", *Chemical Abstracts* 86: 55755f. (1987).

Sindeev, "Study of photopolymerization of oligocarbonate dimethacrylates by a dilatometric method", *Chemical Abstracts*, 103: 215829g. (1986).

Prischepa, "Radiation-induced hardening of oligoetheracrylate and oligocarbonate methacrylate compositions", *Chemical Abstracts*, vol. 94,66593t 1981).

Berlin, "Oligo-Carbonate-Acrylate" *Derwent Abstracts*, No. 80-91804C/51 (1980).

Berlin, "Carbonate-Propargylate", *Derwent Abstracts*, No. 81-90491D/49 (1981).

Waknine et al., "Bond-Strength Characterization of an Experimental Series of Dentin Adhesives," Academy of Dental Materials Meeting, Feb. 18–19, 1988, Chicago, Ill.

Waknine et al., "Characterization of Interfacial Adhesion of a High Strength Porcelain," IADR/AADR Meeting, Mar. 11, 1989, Montreal, P.Q., Canada.

Waknine et al., "Physiomechanical, Adhesion and Cytotoxicity Characterization of Eleven Commercial Dentin Adhesives," AADR Meeting, Paper #1546, Mar. 18, 1989, San Francisco, Calif.

*Primary Examiner*—Mark A. Chapman
*Attorney, Agent, or Firm*—Cummings & Lockwood

[57] ABSTRACT

A polycarbonate dimethacrylate which is the condensation product of 2 parts of hydroxyalkylmethacrylate of the formula.

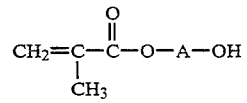

in which A is $C_1$–$C_6$ alkylene, and 1 part of a bis(chloroformate) of the formula (Abstract continued on next page.)

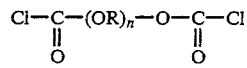

in which R is $C_2$–$C_5$ alkylene having at least two carbon atoms in its principal chain and n is an integer from 1 to 4, is usable, admixed with a secondary monomer suitable for dental applications, such as BIS-GMA; UDMA or the like, as an adhesive system for dental restorative materials. Particularly useful is the novel condensation product of 2-hydroxyethylmethacrylate and triethylene glycol bis(chloroformate).

Dental adhesives containing these components are suitable for application to enamel, pretreated dentin, porcelain and metallic surfaces. The dentin surfaces are pretreated by application of an alcoholic solution of an alkali metal salt of benzene sulfinic acid. The resinous adhesives of the invention can be used in dental compositions which are visible lighting curing, self-curing, dual curing, heat and pressuring curing, or any combination thereof. Where the resinous adhesive is a self-curing adhesive, the polymerization accelerator, which is a tertiary amine such as dihydroxyethyl-p-toluidine, can optionally be incorporated into the alcoholic pre-treatment solution. The condensation product is also suitable for use in filled compositions in which the filler material comprises inorganic silicates.

20 Claims, 2 Drawing Sheets

DENTAL RESIN MATERIALS

CROSS-REFERENCE TO RELATED APPLICATIONS

This is a division of application Ser. No. 07/827,566 filed Jan. 28, 1992 (now U.S. Pat. No. 5,276,068) which is a continuation of application Ser. No. 339,097, filed Apr. 14, 1989, now abandoned, which is a continuation-in-part of application Ser. No. 07/195,351, filed May 12, 1988, now abandoned, which is a continuation of application Ser. No. 06/843,081 filed Mar. 27, 1986, now abandoned, which is a continuation-in-part of application Ser. No. 06/717,332 filed Mar. 29, 1985, now abandoned.

FIELD OF THE INVENTION

This invention relates to polymeric condensation products which have been found to be useful in restorative dentistry. More particularly, it relates to polymeric condensation products which can be used as a principal component of resinous adhesives, and can be used in dental restorative agents. The resinous adhesives of this invention are suitable for bonding to virtually all types of dental surfaces, including enamel, dentin, porcelain and metallic surfaces. They are especially useful in a system for bonding dental restorative materials to exposed dentin. Filled compositions containing the resinous adhesives as components are useful, depending on filler content, as crown and bridge materials either with an alloy substrate or without substrate, as reconstructive materials, bioprostheses, restorative materials, filling materials, inlays, onlays, laminate veneers and the like, as luting agents or cements, and as orthodontic materials, sealants and the like.

BACKGROUND OF THE INVENTION

In recent years, materials used for dental restorations have comprised principally methacrylate polymers. Typical of these polymeric substances are the acrylic resinous materials disclosed in U.S. Pat. Nos. 3,066,112, 3,179,623, 3,194,784, 3,751,399 and 3,926,906. Especially noteworthy is the compound which is the condensation product of bisphenol A and glycidyl methacrylate, 2,2'-bis [4-(3-methacryloxy-2-hydroxy propoxy)-phenyl]-propane (hereinafter abbreviated to "BIS-GMA"). Other methacrylate polymers, such as ethylene glycol dimethacrylate, diethylene glycol dimethacrylate, triethylene glycol dimethacrylate and tetraethylene glycol dimethacrylate, are also in general use as diluents. Polyurethanedimethacrylate is also used as a principal polymer in dental restorative materials of this type. Since BIS-GMA is highly viscous at room temperature, it is generally diluted with a monomer having a lower viscosity such as the aforementioned alkylene glycols or other compatible materials, including trimethylol propyl trimethacrylate, 1,6-hexanediol dimethacrylate, 1,3-butanediol dimethacrylate, and the like.

When these acrylic resinous materials were first developed, they were used unfilled for dental restorative purposes. However, because acrylic materials exhibit high coefficients of thermal expansion relative to the coefficient of thermal expansion for the tooth structure, these unfilled substances soon proved to be less than satisfactory. The disparity in thermal expansion, coupled with high shrinkage upon polymerization, resulted in poor marginal adaptability and ultimately led to secondary decay. Furthermore, the wear and abrasion characteristics and the overall physical, mechanical and optical properties of these unfilled acrylic resinous materials were quite poor. Thus, from the outset, composite dental restorative materials containing these methacrylate resins and fillers were developed. The fillers are generally inorganic filler materials based on silica, silicate glass, or quartz.

Over the years, there have been a number of refinements in the resin matrix component, in the filler component, and in the other additives—notably antioxidants, ultraviolet absorbers, polymerization initiators, polymerization accelerators, etc.—in dental restorative materials. There are now available materials which exhibit high diametral tensile strength, excellent optical properties and polishability, and low water absorption while, at the same time, complying with all of the requirements specified in ADA Specification No. 27 for direct filling resins. Particularly suitable restorative materials are the new compositions having improved inorganic filler materials such as those disclosed in my U.S. Pat. No. 4,547,531, disclosing self-curing 2-component compositions, and U.S. Pat. No. 4,544,359, disclosing visible light curable compositions.

All of these dental restorative materials are required to adhere permanently to the tooth structure. Generally, the tooth surface is treated with an acid such as 30–50 wt. % orthophosphoric acid, which etches the enamel tooth surface and exposes enamel rods in honeycomb prismatic structure thereon, whereby adhesion of the cured polymeric material is improved via micromechanical interlocking. In addition to this process of etching, the prior art teaches the use of various additives and improved monomeric mixtures which are designed to provide improved adhesion.

Although the acid etching technique by itself or coupled with modification of the resinous material to increase adhesive capability has been beneficial in effecting the bonding of dental restorative materials to tooth enamel, there has heretofore been no completely satisfactory process for adhering such restorative materials to dentin. Acid etching is not suitable for bonding dental restorative materials to dentin because the tubular structure of dentin provides passageways to the tooth pulp. The acid can cause great inflammation and pain to the patient and ultimately lead to pulpal necrosis. Furthermore, the high percentage of organic (protein) material in the dentin results in a lower degree of adhesion as compared with enamel.

There has recently been proposed a method for improving adhesion of dental composite materials to dentin surfaces which involves the successive application of (a) an acidic salt such as ferric oxalate or ferric citrate, (b) the adduct of N-(p-tolyl)-glycine and glycidyl methacrylate, the addition reaction product of N-phenylglycine and glycidyl methacrylate or N-phenylglycine itself, and (c) the addition reaction product of pyromellitic acid dianhydride and 2-hydroxyethylmethacrylate, the addition reaction product of 3,3',4,4'-benzophenonetetracarboxylic dianhydride and 2-hydroxyethylmethacrylate, or 4-methacryloxyethyltrimellitic anhydride. This multi-step process has, however, not proved satisfactory.

In addition to much desired improvements in dentin bonding systems, it is also desirable to attain improved bonding to other dental surfaces, such as enamel, alloy-substrates and, particularly porcelain.

Despite recent advances in the development of filled dental restorative materials which have led to composites having higher resistance to abrasion, better handling characteristics, and more satisfactory visual appearance, there remains considerable room for improvement in these areas. Specifically desired are improved filled compositions for use as crown and bridge materials, denture-base materials, luring agents or cements and orthodontic appliance materials and sealants.

Accordingly, it is one primary object of this invention to provide improved dental adhesive materials for bonding to dentin, enamel, metallic alloys and porcelain.

It is another primary object of this invention to provide improved filled compositions for use as luring agents, denture-base materials, orthodonic materials and sealants, crown and bridge materials and other dental restorative materials.

It is a further object of this invention to provide a method for bonding a dental restorative material to a properly prepared tooth surface including dentin, enamel metallic alloys and porcelain.

Other objects include the provision of a dentin bonding system which employs a non-irritating pretreatment to yield a proper surface for application of the dental adhesive.

Still another object is to provide improved a dental adhesive which is particularly suitable for bonding to a properly prepared dentin surface. Other objects of this invention will become apparent from the following specification.

SUMMARY OF THE INVENTION

This invention provides resinous dental compositions comprising polycarbonate dimethacrylate condensation products as a principal component, and a secondary monomer such as BIS-GMA or urethane dimethyacrylate or the like as a second component, which is provided to impart strength to the dental composition. The resinous dental composition can additionally include a third, diluent monomer to increase the surface wettability of the resinous matrix.

The polycarbonate dimethyacrylate condensation products of the invention result from the condensation, under carefully controlled conditions, of two parts by weight of a hydroxyalkylmethacrylate of the formula I

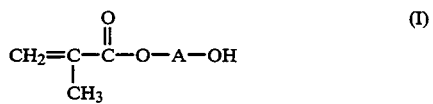

in which A is $C_1-C_6$ alkylene, and one part by weight of a bis(chloroformate) of the formula II

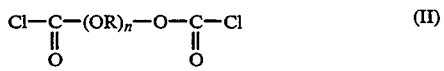

in which R is $C_2-C_5$ alkylene having at least two carbon atoms in its principal chain and n is an integer from 1 to 4. Of particular interest is the novel condensation product of 2-hydroxyethylmethacrylate and triethylene glycol bis(chloroformate).

The new dental compositions which are unfilled, constitute one embodiment of the dental adhesive materials of this invention. These dental adhesives can be applied to all types of dental surfaces, including enamel, dentin, porcelain and metallic surfaces but are particularly suited for application to pretreated dentin surfaces.

In addition to the unfilled resinous adhesive compositions, there are also provided, in another embodiment, filled compositions comprising the new polycarbonate dimethacrylate condensation products as a principal component, together with the secondary monomer and various inorganic additives and/or fillers. Such filled compositions are useful for a variety of dental treatments and restorative functions including crown and bridge materials, luring agents or cement denture-base materials, orthodontic materials and sealants, and dental restorative materials.

The resinous dental compositions of this invention include visible light curable, self-curing, dual curing, and heat and pressure curble compositions as well as any combination thereof. The visible light curable compositions include, in addition to the polycarbonate dimethacrylate condensation product and the second monomeric component, the usual polymerization initiators, polymerization accelerators, ultraviolet absorbers, fluorescent whitening agents, and the like. In the self-curing compositions, the polymerization accelerator can be included in the resinous composition itself or can be present in a liquid composition which is used for pretreating the exposed dentin. The heat and pressure curable compositions, which are generally filled compositions, include, in addition to the monomeric components, a heat cure initiator such as benzoyl peroxide.

This invention also provides a method for bonding dental restorative material to properly prepared tooth surfaces including enamel, porcelain or metal. The method comprises applying to the surface the new, unfilled dental composition of the present invention causing the dental composition to cure and placing the restorative material on the cured surface.

This invention also provides methods for bonding dental restorative materials to an exposed dentin surface. The surface can be pretreated by application of 3% $H_2O_2$, 17% EDTA or 5% NaOCl in non-vital teeth followed by an alcohol or acetone solution of an alkali metal salt of benzenesulfinic acid with subsequent evaporation of the alcohol from the solution. Alternatively, the surface can be pretreated by first applying an alcohol or acetone solution of an alkali metal salt of benzenesulfinic acid and then applying an acetone solution of N-phenyl-glycine. The treated dentin surface is then coated with a resinous adhesive according to this invention. The adhesive is then cured and an appropriate dental restorative material is applied. Where the adhesive is a self-curing composition, the polymerization accelerator can either be included in the adhesive itself or be incorporated into the alcohol or acetone pretreatment solution, in which case the accelerator remains on the dentin surface after evaporation of the solvent.

BRIEF DESCRIPTION OF THE DRAWINGS

The present invention will become more readily understood by reference to the drawings which illustrate one aspect of the present invention.

DETAILED DISCLOSURE

Figure 1:
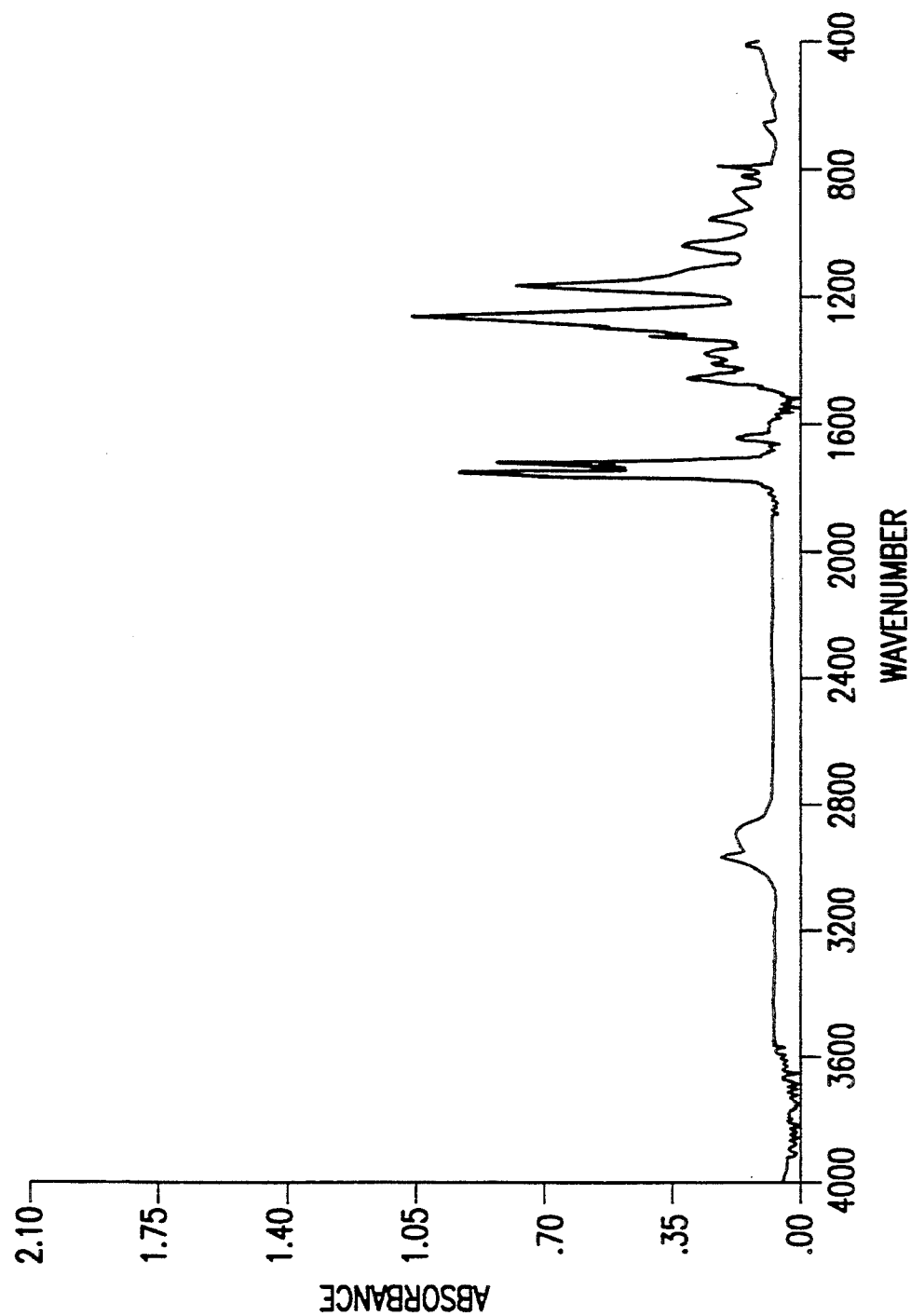
FIG. 1 is a graphical representation of the infrared spectrophotometric analysis of the novel polycarbonate dimethacrylate obtained in accordance with Example 1.

The polycarbonate dimethacrylate condensation products usable in this invention are obtained by the condensation reaction of an hydroxyalkylmethacrylate of the general formula I

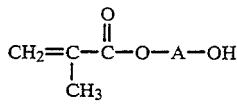

in which A is $C_1$–$C_6$ alkylene, and a bis(chloroformate) of the general formula II

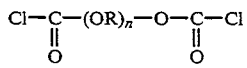

in which R is $C_2$–$C_5$ alkylene having at least two carbon atoms in its principal chain and n is an integer from 1 to 4. By "principal chain" is meant the chain of carbon atoms serving as a bridge between the oxygen atoms.

In the hydroxyalkylmethacrylate, the group A can be, for example, methylene, ethylene, propylene, 2,2-dimethylpropylene, butylene, and the like. Preferred compounds are those in which A has 2 or 3 carbon atoms, such as 2-hydroxyethylmethacrylate and 2-hydroxypropylmethacrylate, with 2-hydroxyethylmethacrylate particularly preferred. In the bis(chloroformate), examples of the group R include ethylene, 1-methylethylene, 1,2-dimethylethylene, propylene, 2-methylpropylene, 2,2-dimethylpropylene, butylene, and the like. The preferred groups for R are ethylene, propylene, and with them the preferred values for the integer n are 2 and 3. Particularly preferred as the bis(chloroformate) reactant is triethyleneglycol bis(chloroformate)

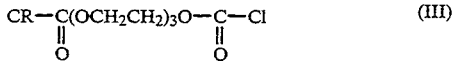

but others, such as diethylene glycol bis(chloroformate), tetraethylene glycol bis(chloroformate), dipropylene glycol bis(chloroformate) and tripropylene glycol bis(chloroformate) are also quite suitable. In general, the bis(chloroformates) for use in the practice of this invention include those of the aforementioned generic formula which are liquid at temperatures employed in the condensation reaction.

The hydroxyalkylmethacrylates and the various bis(chloroformates) required as starting materials for the polycarbonate dimethacrylate condensation products are either available commercially or can be easily prepared by known methods. The bis(chloroformate) starting materials can be prepared, for example, by reaction of phosgene with the appropriate glycol according to methods well known in the art. Triethylene glycol bis(chloroformate) and certain other bis(chloroformates) can be obtained from PPG Industries (Chicago, Ill.).

The polycarbonate dimethacrylate condensation products are prepared by reacting two moles of the hydroxyalkylmethacrylate and one mole of the bis(chloroformate). Said condensation products have the general formula IV

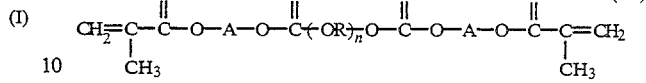

in which A, R and n are as defined above.

The preferred polycarbonate dimethacrylate condensation products are those which, based on Formula IV, have a molecular weight between about 400 and about 550, preferably between about 418 and about 506. Particularly preferred is the novel polycarbonate dimethacrylate obtained with triethylene glycol bis(chloroformate) and 2-hydroxyethylmethacrylate, which has the formula V

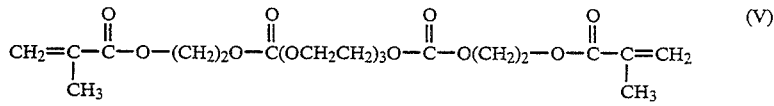

with a molecular weight of 462.

The polycarbonate dimethacrylate condensation product is obtained by adding the bis(chloroformate) slowly by drop-wise addition to the hydroxyalkylmethacrylate in a suitable solvent such as pyridine. The solution should be well stirred during the condensation reaction and the temperature should be maintained between about $-5°$ C. and $10°$ C., preferably between about $-2°$ C. and $4°$ C. Conveniently, the reaction can be conducted in an ice bath, thus maintaining a temperature of about $3°$ C. to $4°$ C. These low temperatures are necessary in order to prevent polymerization. After the condensation reaction is complete, the product is separated from solvent, unreacted starting materials, and by-products by methods well known in the art.

Many of the condensation products included within the scope of formula (IV) are known from U.S. Pat. No. 3,716,571 issued Feb. 13, 1973, and from Soviet Author's Certificate No. 732,291 published on May 8, 1980. They have heretofore found utility as binder compositions in glass-reinforced plastics, electric insulating compositions, heat resistant compositions, and the like. The specific condensation product of triethyleneglycol bis(chloroformate) and 2-hydroxyethylmethacrylate is a novel substance.

Aromatic polycarbonates derived from bisphenol-A by reaction with diphenyl carbonate or phosgene are known products and have been used as denture-base materials; see Stafford et al, "Polycarbonates: A Preliminary Report on the Use of Polycarbonates as a Denture Base Material", *Dental Practitioner* 17, 217–23 (1967). In contrast to the relatively low molecular weight condensation products usable in this invention, these previously-described polycarbonates have phenylene groups rather than the alkylene groups and have preferred molecular weights in the range of 30,000 to 200,000.

The polycarbonate dimethacrylate condensation products of the present invention are relatively ductile materials which require the addition of a strengthening component to achieve excellent properties as a dental composition. Therefore, the resinous dental compositions of the present invention include, in addition to the polycarbonate dimethacrylate condensation products, a second monomeric material which is added to impart strength to the resulting resin matrix.

The secondary monomer can be selected from previously known monomers suitable for dental applications, including the epoxys, phenolic epoxys, methacrylates, acrylates, isocyanates and reaction products thereof. These materials will generally be more brittle and of higher viscosity than the polycarbonate dimethacrylate condensation products. Typical of such materials are those hereinbefore referenced. The most commonly employed monomers are generally monomeric methacrylic esters. Because of an excellent combination of physical properties, i.e. dimetral tensile strength, water sorbtion index of refraction, shrinkage, lack of toxicity and/or biocompatibility, the secondary monomer is preferably a monomer such as a methacrylate, polyurethane or the like. The preferred monomeric materials are BIS-GMA and urethane dimethacrylate (hereinafter abbreviated UDMA), and derivatives and oligomers thereof, with BIS-GMA being the most preferred.

Suitable derivatives of BIS-GMA include, but are not limited to ethoxylated derivatives, phosphate and/or chlorophosphate derivatives and carbamate derivatives, and oligomers thereof. Suitable derivatives of UDMA include the diisocyanate derivatives and oligomers thereof.

In addition to the two aforementioned monomeric components, the resinous dental compositions of the present invention can further include a diluent monomer to increase the surface wettability of the composition by decreasing the viscosity of the polymerization medium and increasing the contact angle of the droplet. Suitable diluents include hydroxyalkyl methacrylates, such as 2-hydroxyethylmethacrylate and 2-hydroxypropylmethacrylate; ethyleneglycolmethacrylates, including ethyleneglycolmethacrylate, diethyleneglycolmethacrylate, triethylene glycolmethacrylate and tetraethyleneglycolmethacrylate; diisocyanates, such as 1,6-hexamethylene diisocyanate ethoxylated monomers such as 1,6-hexanedioldimethacrylate, 2-hydroxyethylmethacrylate is particularly preferred.

The subject polycarbonate dimethacrylates are suitable for incorporation into dental compositions, including those which are visible light curable, those which are self-curing and those which are both self curing and visible light curing. Typically, these polycarbonate dimethacrylates are incorporated into a resinous composition having from about 30 to about 80 weight percent of the polycarbonate dimethacrylate, from about 5 to about 60 weight percent of the secondary monomer, such as BIS-GMA or UDMA, and from about 0 to about 50 weight percent of a diluent monomer, such that the specific amounts within these ranges yields a 100% by weight polymerization system. When no diluent component is employed the preferred ranges for the secondary monomer are 25 to 35 weight percent, particularly about 30 weight percent, and the preferred ranges for the polycarbonate dimethacrylates are from 65 to 75 weight percent, particularly about 70 weight percent. The diluent, when employed, is preferably included in an amount of 20-40 weight percent, with the PCDMA present in an amount of about 40 to 72 weight percent, and the secondary monomer in an amount of about 15.35 weight percent.

In addition to these materials, the resinous compositions of this invention can also typically include polymerization initiators, polymerization accelerators, ultraviolet light absorbers, anti-oxidants, and other additives well known in the art. Although a polymerization initiator and a polymerization accelerator are generally used in the resinous adhesive compositions, the presence of a polymerization accelerator in the self-curing adhesive compositions of this invention is optional. One of the features of the self-curing dentin bonding system of this invention is that the polymerization accelerator can be incorporated into the dentin pretreatment composition rather than into the resinous adhesive composition.

The polymerization initiators usable in the resinous adhesives of this invention are conventional initiators known in the art. For example, visible light curable compositions employ light-sensitive compounds such as benzil, diketones and in particular, dl-camphoroquinone in amounts ranging from about 0.05 to 0.5 weight percent. Self-curing compositions will generally contain free radical polymerization initiators such as, for example, a peroxide in amounts ranging from about 2 to about 6 weight percent. Particularly suitable free radical initiators are lauroyl peroxide, tributyl hydroperoxide and, more particularly benzoyl peroxide.

The polymerization accelerators usable in the compositions of this invention are the various organic tertiary amines well known in the art. In visible light cured compositions, the tertiary amines are generally acrylate derivatives such as dimethylamino ethylmethacrylate and, particularly, diethylamino ethylmethacrylate in amounts ranging from about 0.05 to about 0.5 weight percent. In the self-curing compositions, the tertiary amines are generally aromatic tertiary amines, such as dimethyl-p-toluidine, dihydroxyethyl-p-toluidine, and the like, in amounts ranging from about 0.05 to about 4.0 weight percent. These can optionally be incorporated in a pretreatment solution rather than in the resinous adhesive.

It is preferred also to employ an ultraviolet absorber in these resinous adhesives in amounts ranging from about 0.05 to about 5.0 weight percent. Such UV absorbers are particularly desirable in the visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Typical visible light curable resinous dental compositions according to this invention comprise:
- 65–75 weight percent of the polycarbonate dimethacrylate condensation product of triethylene glycol bis(chloroformate) and 2-hydroxyethylmethacrylate,
- 25–35 weight percent of BIS-GMA,
- 0.05–0.35 weight percent of dl-camphoroquinone,
- 0.05–0.5 weight percent of diethylamino ethylmethacrylate, and
- 0.05–5 weight percent of TINUVIN P ultraviolet absorber.

in specific amounts within these ranges to yield a 100% by weight polymerization system.

Typical resinous compositions for use in self-curing systems comprise a catalyst component comprising:
- 65–75 weight percent of the polycarbonate dimethacrylate condensation product of triethylene glycol bis(chloroformate) and 2-hydroxyethylmethacrylate, 25-35 weight percent of BIS-GMA, 0.2-5.0 weight percent of benzoyl peroxide, and 0.05-4.5 weight percent of TINUVIN P ultraviolet absorber.

0.01-0.250 BHT inhibitor; and a base or accelerator component comprising:

65-75 weight percent of the polycarbonate dimethacrylate condensation product of triethylene glycol bis(chloroformate) and 2-hydroxyethylmethacrylate, 25-35 weight percent of BIS-GMA, 0.020-0.200 weight percent of BHT, and 0.2500-1.7500 weight percent of dihydroxyethyl-p-toluidine.

in specific amounts within these ranges to yield a 100% by weight polymerization system.

It is also possible to use the polycarbonate dimethacrylate condensation products in resinous compositions which are both self-curing and visible light curable. In this "combination" or dual cure system the resinous adhesive composition is similar to the visible light curable composition described above with the addition of about 0.2 to about 5.0 weight percent of benzoyl peroxide and the omission of the diethylaminoethylmethacrylate in the dual cure composition. The liquid base component of the dual cure system includes ethanol or acetone in an amount of about 98.20 weight percent, about 0.2500 weight percent of dihydroxyethyl-p-toluidine self-cure accelerator, about 0.2300 weight percent of diethylamino-ethylmethacrylate visible light cure accelerator and optionally contains about 1.3300 weight percent sodiumbenzene sulfinic acid salt.

In one preferred embodiment of the present invention, the resinous dental composition further comprises a diluent monomer, such as 2-hydroxyethylmethacrylate (2-HEMA). In a visible light curable composition including 2-HEMA, the resulting overall compositions in weight percent comprise:

| Broad Range | Preferred Range | Most Preferred | Component |
|---|---|---|---|
| 30-80 | 40-72 | 50 | Polycarbonate dimethacrylate condensation product of triethylene glycol bis(chloroformate) and 2-HEMA |
| 5-60 | 15-35 | 20 | BIS—GMA |
| 0-50 | 20-40 | 30 | 2-HEMA |
| 0.05-0.40 | .200-.300 | 0.23 | diethylaminoethylmethacrylate |
| 0.25-4.0 | .5000-1.500 | 1.0 | TINUVIN P 6.0 ultraviolet absorber |
| 0.05-.50 | .1000-.25000 | 0.1650 | 2,3-d-borandione or d,l-camphoroquinone |
| 0.00 | 0.00 | 0.0741 | BHT |
| 00.2500 | 0.1500 | | |
| 0.00 | 0.00 | 0.0097 | Fluorescent/whitinging agent, e.g. UNITEX OB |
| 0.500 | 0.2500 | | | in specific amounts within these ranges to yield a 100% by weight polymerization system.

A diluent, such as 2 hydroxyethylmethacrylate, is also preferably employed in the self-cure and dual-cure resinous dental compositions in an amount of up to 50 weight percent.

In addition to unfilled compositions, the dental compositions of the present invention can also be filled or partially filled. The filled compositions of this invention can include all of the inorganic fillers currently used in dental restorative materials, the amount of such filler being determined by the specific function of the filled materials. Thus, for example, where crown and bridge materials are being prepared, the resinous compositions of the present invention are present in amounts ranging from about 20 to about 40 weight percent, and the filler materials are present in amounts ranging from about 60 to about 80 weight percent. Typical compositions for crown and bridge materials are about 25% of the resinous material and about 75% of the filler. For luting cements, the resinous compositions of this invention are present in amounts ranging from about 27 to about 70 weight percent, the fillers comprising from about 30 to about 73 weight percent. For orthodontic sealant and orthodontic cement compositions, there will typically be from about 90 to about 100% of resinous component and about 0 to about 10% of filler.

The filled compositions of this invention can, in general, include any suitable filler which is capable of being covalently bonded to the resin matrix itself or to a coupling agent which is covalently bonded to both. Examples of suitable filling materials include but are not limited to, silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide and titania. Particularly suitable as fillers for dental restorative materials prepared in accordance with this invention are those having a particle size ranging from about 0.1-5.0 um with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. Nos. 4,544,359 and 4,547,531, pertinent portions of which are incorporated herein by reference. One consideration in the selection of a filler is the difference in the index of refraction of the filler material and that of the resinous matrix. In general, a more aesthetically pleasing restoration can be obtained when the difference between the index of refraction of the filler material and that of the resin matrix is small.

As with the unfilled compositions, the filled and partially filled compositions can be prepared in visible light curable formulations self-curing, and dual curing formultions. In addition, the filled compositions can be prepared in heat pressure curing formulations. It has surprisingly been found that heat-pressure curing the filled or partially filled dental compositions of the present invention results in a material which exhibits superior physical and mechanical propereties when compared to other modes of cure. The filled composite restorative materials can be prepared by admixing from about 20 to 30% by weight, preferably 20-26% by weight, of the unfilled visible light curable self curing, dual-curing or heat-pressure curable composition dental composition with from about 65 to about 85% by weight, preferably about 75 to 83% by weight of inorganic filler material.

The composite dental restorative material of the present invention preferably comprises an inorganic filler having an average particle size diameter of from about 0.5 to 5 microns homogeneously dispersed in an organic polymerizable monomeric matrix comprising a polycarbonate dimethacrylate. In addition, a relatively small amount of fumed silica is also predispersed within the monomeric matrix. The inorganic filler primarily comprises an X-ray opaque alkali metal or alkaline earth metal silicate such as lithium alumina silicate, barium silicate, strontium silicate, barium borosilicate, strontium borosilicate, borosilicate, as well as any of the aforementioned materials. For purposes of illustration, and as the preferred silicate species, barium borosilicate will hereinafter be employed as being typical of the alkali metal or alkaline earth metal silicates which can be suitably employed in the present invention. The barium borosilicate exhibits an index of refraction close to that of the organic monomeric matrix in which it is dispersed. The filler can additionally contain a relatively small amount of borosilicate glass which imparts greater compressive strength to the resulting composite and enhances the translucency thereof thereby enabling better blending of the restorative material with the adjacent teeth. In addition, the presence of the borosilicate glass helps narrow the gap in the mismatch of refractive indices between the barium borosilicate inorganic fiber phase and the organic monomeric matrix.

The ability to provide a composite dental material having improved properties is achieved by the method by which the inorganic filler is prepared. This method involves a sequence of milling operations which includes wet milling to reduce the barium borosilicate and borosilicate to the requisite particle size and assure a very narrow particle size distribution and to uniformly disperse the borosilicate glass particles throughout the bulk of the barium borosilicate. Thereafter, the wet milled filler is subject to a further milling operation to microetch the surface thereof which has been found to impart a dramatic increase to the dimetral tensile strength of the resulting composite. Subsequently, the so treated filler is subjected to a final milling operation during which it is silanated in order to render it compatible with the resin in which it will ultimately be dispersed.

Details of the preparation of the inorganic filler, which comprises a mixture of from about 5 to about 20% by weight of borosilicate glass and from about 80 to about 95% by weight barium borosilicate, and has an average particle size diameter of from about 0.5 to about 5 microns, can be found in the aforementioned U.S. Pat. Nos. 4,544,539 and 4,547,531.

This invention also includes methods for bonding dental restorative materials to various surfaces, such as enamel, porcelain, metallic alloy and particularly to exposed dentin surfaces. For such dentin surfaces, the methods include pretreatment of the dentin surfaces and coating of the treated surfaces with the resinous adhesive compositions of this invention.

When dentin surfaces are exposed as a result of cutting and abrasion which occurs during treatment, there is formed on the dentin surface a "smear layer" composed principally of organic material. This smear layer is believed to cause partial filling of the dentin tubules as well as to obstruct the orifices of said tubules. Pretreatment of the dentin surface can be preceded by removal of the smear layer. It has been found that this smear layer is readily removed by application, for example, of a 5 percent aqueous solution of sodium hypochlorite, a 17 percent aqueous solution of ethylenediaminotetraacetic acid tetrahydrate sodium salt or a 6 percent citric acid gel. Prior removal of the smear layer is optional in the present invention, since essentially equivalent strengths can be obtained without removal thereof.

In applying the resinous adhesive compositions of this invention to dentin surfaces, the first step after the usual prophylaxis with, for example, flour of pumice or 3% hydrogen peroxide, is a pretreatment of the dentin surface with an alcohol or acetone solution containing an alkali metal salt of benzenesulfinic acid, preferably sodium benzenesulfinate salt. Preferred alcohols include ethanol, methanol and isopropyl alcohol. If the dental restorative composition to be used is a self-curing composition, the alcohol or acetone pretreatment solution for the dentin can also include an organic tertiary amine polymerization accelerator, preferably an aromatic amine such as dihydroxyethyl-p-toluidine. Typical alcohol solutions for use in this pretreatment contain from about 0.1 to about 5 weight percent of sodium benzenesulfinate, and from about 0.1 to about 2.5 weight percent of dihydroxyethyl-p-toluidine, the remainder being alcohol, such as ethanol. In one preferred embodiment of the present invention, an acetone solution for use in this pretreatment contains from about 0.1 to about 4.0 weight percent of sodium benzenesulfinate, preferably about 1.30 weight percent of sodium benzenesulfinate.

The alcohol or acetone solution is applied to the dentin surface and is then evaporated. Evaporation can be effected by a dry air stream or other methods well known in the art. This pretreatment step fulfills the function of (1) prophylaxis and (2) improving the dentin surface for acceptance of the resinous adhesive. The benzenesulfinic acid salt causes a chelating polymerization promotion of the dentin surface with the adhesive and results in partial filling of the tubules of the dentin. Thus, the dentin surface is made considerably more susceptible for enhanced adhesion. This enhanced surface roughness is obtained without the use of irritating substances such as phosphoric acid.

If the alcohol solution also contains an aromatic tertiary amine, this is deposited on the surface of the dentin and functions as a polymerization accelerating agent when a resinous adhesive, without accelerator, is applied in the third step. In one preferred embodiment of the present invention wherein the alcohol or acetone solution of sodium benzenesulfinate is employed without an aromatic tertiary amine, a second pretreatment comprising an acetone solution containing from about 0.10 to about 20, preferably about 10.0, weight percent N-phenyl-glycine (98–99% purity) in acetone accelerates the reaction between the N-phenyl-glycine and the glycoprotein component of the dentin resulting in a peptide bond therebetween.

The resinous adhesive compositions of this invention are then coated onto the pretreated dentin surface, according to methods well known in the art. If the resinous adhesive composition is a light curable composition, polymerization is effected by exposure to a visible light source, for example a 150 watt halogen light source or any visible light source which is capable of generating light within wavelengths ranging from about 250 to about 750 nanometers, preferably from 450 to 500 nanometers and more preferably from 468 to 492 nanometers, for about 20 to 50 seconds. If the resinous adhesive composition is a self-curing composition, a period of about 3 to 6 minutes should be allowed for polymerization.

The dental composition of this invention is also suitable for use on a properly prepared enamel surface and can be simultaneously applied to a pretreated dentin surface and adjacent areas of an enamel surface. Such enamel surfaces can be subjected to etching treatment with, for example, 30–50 wt. % orthophosphoric acid. Obviously, steps should be taken to shield the exposed dentin from the enamel etching treatment.

The compositions of this invention can be employed in the following manner as a dentin adhesive bonding system where the smear layer has been removed from the dentin surface and adjacent exposed enamel has been acid etched by the use of well-known etching materials such as, for example, orthophosphoric acid gel. Pulp protection is accomplished by use of, for example, a calcium hydroxide composition.

After scraping any debris from the dentin surface, it is cleaned with an oil-free dental pumice and water. A 3% hydrogen peroxide solution is then applied as prophylaxis and the dentin surface is washed and dried.

The restoration site is then isolated with a Mylar polyester strip for proper gingival margins, gingival pappilae and adjacent tooth preparation via sliding preshaped/formed contour strips into gingival sulcus. The polyester strips can be tightened to seal the gingival margin, thus isolating saliva and gingival crevicular fluid flow to the restored area. In addition, dental wedges are recommended in order to separate teeth, facilitate interproximal contact and hold the polyester strips in position. Two or three drops of a liquid solution of sodium benzene sulfinate in alcohol or acetone are brushed over the dentin surface. If a self-curing adhesive system is used, this solvent solution can additionally contain dihydroxy-p-toluidine. The alcohol or acetone should be permitted to evaporate, with air drying recommended for this purpose.

Optionally, two or three drops of a liquid solution of N-phenyl-glycine in acetone are brushed over the pretreated dentin surface and again, the acetone permitted to evaporate, preferably with air drying.

The resinous adhesive composition is then applied over the etched peripheral enamel beyond cavo-surface margins and over the dry, prepared and conditioned dentin surfaces. An extremely thin layer of resinous adhesive is obtained by removing excess material from enamel and dentin surfaces with a dry brush and jet of oil-free and moisture-free air. If the adhesive composition is visible light curable, it should be exposed to a visible light source such as, for example, a Spectra-Lite, light source available from Jeneric/Pentron, Inc. of Wallingford, Conn. for about 40 seconds. If a self-curing adhesive composition is used—with the polymerization accelerator either on the pretreated dentin surface or in the resinous adhesive itself—a period of about three to five minutes should be allowed for polymerization. Immediately, thereafter, the dental restorative material should be placed onto the adhesive. Alternatively, the restorative material and the adhesive can be cured simultaneously.

In addition to use for bonding restorative materials in situations where exposed dentin is encountered, the resinous dental compositions of this invention are also applicable for the bonding of enamel, porcelain and metallic alloys, each to each other, or for the bonding of other dental restorative materials, including all types of acrylic base materials and various crown and bridge alloy compositions, to enamel, porcelain and metallic surfaces. The resinous dental compositions are applied to the surfaces to be adhered by methods well known in the art. Typically, the surfaces are prepared by, for example, etching or sand blasting.

The unfilled dental materials of the present invention are also particularly suitable for promoting the adhesion of various dental restorative materials to porcelain surfaces. Generally, the porcelain surface is etched by, for example, hydrofluoric acid and the resinous adhesive compositions of this invention applied to the etched surfaces. The adhesive is then cured by methods well known in the art such as, for example, visible light curing, self curing or dual curing. If, visible light curing is desired, the adhesive composition should also contain the various visible light curing additives discussed above. The dental restorative material is then applied to the cured adhesive. Such restorative materials include virtually all of the materials currently used in dentistry and can also include the novel filled compositions of this invention.

When using the resinous compositions of this invention as a porcelain adhesive, it is preferred that there be a silane coupling agent used between the etched surface of the porcelain and the resinous adhesive composition. The silane coupling agent is brushed onto the etched porcelain surface prior to application of the resinous adhesive. Useful silane coupling agents can be selected from members of organosilicon monomers such as aminoalkyl(trisalkoxy) silanes which are characterized by the formula R—SiX$_3$, wherein R is an organofunctional group attached to silicon in a hydrolytically stable manner and X designates hydrolyzable groups which are converted to silanol groups upon hydrolysis. Most commonly, R comprises a 3-aminopropyl or 3-ureidopropyl moiety which may be further separated from the silicon group by one or two —NH(CH$_2$)—$_n$ moieties wherein n=1-2. Preferably X is an alkoxy group selected from the group consisting of methoxy, ethoxy, 2-methoxyethoxy or is acetoxy, specifically -methacryloxypropyltrimethoxysilane, A-174 available from Union Carbide. Preferred silane coupling agents are commercially available from Union Carbide as the A1100-A1160 series which includes 3-aminopropyltri-ethoxysilane, 3-aminopropyltrimethoxysilane (also available from Dow Corning as Z-6020), N-2 aminoethyl-3-aminopropyltrimethoxysilane, or 3-ureidopropyltriethoxysilane.

This invention will be better understood by reference to the following examples which are included here for illustrative purposes only and are not to be construed in limitation of the claims.

EXAMPLE 1

Preparation of Condensation Product of
2-Hydroxyethylmethacrylate and Triethylene Glycol
bis(Chloroformate)

(A) The apparatus used was a round-bottom flask containing a magnetic stirring bar and fitted with an addition funnel and drying tube; said apparatus was fitted on an ice bath and stirring plate. 110 ml of pyridine was poured into the flask and 78.86 grams of 2-hydroxyethylmethacrylate (0.606 moles) was slowly added. To this was added very slowly—over a period of about two hours—82.5 grams (0.300 moles) of triethylene glycol bis(chloroformate). A white precipitate began forming almost immediately. After the addition was completed, the ice bath was removed and the mixture allowed to stir overnight at room temperature.

(B) The mixture was then slowly added to 77 ml of concentrated hydrochloric acid containing about 120 g of ice.

(C) The mixture from Step (B) was placed in a separatory funnel and oil and aqueous/acid layers were separated. The aqueous/acid layer was extracted twice with 150 ml of ethyl acetate (total 450 ml). The oil layer and the ethyl acetate extractants were combined into an organic layer.

(D) The organic layer was washed five times with 100 ml of 1 molar HCl, once with 100 ml of water, twice with 100 ml of 5% NaOH, once with 100 ml of water, and once with 100 ml of saturated NaCl solution. The product was then dried overnight with $MgSO_4$.

(E) The dried product was decolorized with Carbon Norite and filtered by gravity filtration. The solvent was removed on a roto-evaporator at a temperature of 40° C. and the product, a clear water white solution was obtained. 0.03% of 2,6-di-tert.butyl-4-methylphenol was added as a polymerization inhibitor.

(F) An IR spectrum and size exclusion chromatographic plot shows the molecular weight to be 462.

(G) The product thus obtained was subject to a chemical analyses, including infrared spectrophotometry, (IR), nuclear magnetic resonance spectrophotometry (NMR), and refractive index analysis on a Bausch & Lomb refractometer, each of which confirmed structure of the product as being the condensation reaction product of 2-hydroxyethylmethacrylate and one mole of triethylene glycol bis(chloroformate).

FIG. 1 is a plot from an infrared spectrophotometric analysis performed on a polycarbonate dimethacrylate prepared in accordance with this Example. The plot is of the absorption intensity vs. wavenumber, and is illustrative of the relative strengths and positions of the absorbtions in the infrared region.

Figure 2:
FIG. 2 is a graphical representation of the Nuclear Magnetic Resonance spectrophotometric analysis of the novel polycarbonate dimethacrylate obtained in accordance with Example 1.

FIG. 2 is a plot from a proton nuclear magnetic resonance analysis performed on a polycarbonate dimethacrylate prepared in accordance with Example 1, with deuterated carbon tetrachloride and tetramethylsilane (TMS) as the reference solvent. The E spectrum is a plot of the strength of the magnetic field versus the intensity of the absorbtion.

EXAMPLES 2–15

In like manner, the following additional polycarbonate dimethacrylates were prepared.

| EXAMPLE NO. | —A— | —(OR)$_n$— | Mol. Wt. |
|---|---|---|---|
| 2 | $CH_2$ | $(OCH_2CH_2)_3$ | 434 |
| 3 | $CH_2CH_2CH_2$ | $(OCH_2CH_2)_3$ | 490 |
| 4 | $CH_2CH_2$ | $(OCH_2CH_2)_2$ | 418 |
| 5 | $CH_2CH_2$ | $(OCH_2CH_2)_4$ | 506 |
| 6 | $CH_2$ | $(OCH_2CH_2CH_2)_3$ | 504 |
| 7 | $CH_2$ | $[COCH(CH_3)CH_2]_2$ | 418 |
| 8 | $CH_2$ | $(OCH_2CH_2)_4$ | 478 |
| 9 | $CH_2$ | $(OCH_2CH_2CH_2CH_2)_4$ | 446 |
| 10 | $CH_2CH_2$ | $[OCH_2CH(CH_3)CH_2]_2$ | 474 |
| 11 | $CH_2$ | $(OCH_2CH_2CH_2CH_2CH_2)_2$ | 474 |
| 12 | $CH_2$—$CH_2$ | $[OCH_2C(CH_3)_2CH_2]_2$ | 502 |
| 13 | $CH_2$—$CH_2$—$CH_2$—$CH_2$ | $(OCH_2CH_2)_2$ | 474 |
| 14 | $CH_2$—$CH(CH_3)$ | $(OCH_2CH_2)_2$ | 446 |
| 15 | $CH_2$—$CH(CH_3)$ | $(OCH_2CH_2CH_2)_2$ | 474 |

EXAMPLE 16

Self-Curing Dentin Adhesive Bonding System

A two-component self-curing dentin adhesive bonding system having the following constituents was prepared. The first component is a liquid composition having:
 95.60 grams of ethanol,
 4.00 grams of sodium benzene sulfinate, and
 0.40 grams of dihydroxyethyl-p-toluidine.
The second component is a resin composition having:
 70.96 grams of a polycarbonate dimethacrylate which is the condensation reaction product of 2-hydroxyethylmethacrylate and triethylene glycol bis(chloroformate),
 29.03 grams of BIS-GMA,
 0.0373 grams of 2,6-ditert.butyl-4-methylphenol (inhibitor),
 0.75 grams of TINUVIN P (ultraviolet absorber from Ciba-Geigy Corporation, Ardsley, N.Y.),
 4.00 grams of benzoyl peroxide (initiator), and 0.0097 grams of UTITEX OB (fluorescent whitening agent from Ciba-Geigy Corporation, Ardsley, N.Y.).

The liquid composition is used as a pretreatment for exposed dentin surfaces, while the resin composition is an example of a resinous adhesive according to this invention.

EXAMPLE 17

Dual-Curing Dentin Adhesive Bonding System

A two-component dual-curing dentin adhesive bonding system was prepared, whose first component was identical to the liquid component of Example 16, except that 0.2300 gm diethylamino ethylmethacrylate was added in the dual curing liquid component. The second component was identical to the second component of Example 16 except that 0.1650 g d,l-camphoroquinone and 3.0 gm BPO, instead of 4.0 gm BPO, were added.

EXAMPLE 18

Visible Light Curable Dentin Adhesive Bonding System

A three-component visible light curable dentin adhesive bonding system having the following constituents was prepared.

The first component was a liquid composition comprising:
 98.70 grams of acetone, and
 1.30 grams of sodium benzenesulfinate.

The second component was also a liquid composition comprising:
 10.00 grams of N-phenyl-glycine (97.0–98.5% purity), and
 90.00 grams of acetone.

The third component was a resinous composition, comprising:

50 grams of a polycarbonate dimethacrylate which is the condensation reaction product of 2-hydroxyethylmethacrylate and triethylene glycol bis(chloroformate),
20.0 grams of BIS-GMA
30.0 grams of 2-hydroxyethylmethacrylate,
0.2300 grams of diethylamino ethylmethacrylate,
0.1650 grams of d,l-camphoroquinone,
0.0743 grams of benzoylhydroxytoluidine (BHT),
1.000 grams of TINUVIN P (ultraviolet absorber from Ciba-Geigy Corporation, Ardsley, N.Y.),
0.0097 grams of UVITEX OB (fluorescent whitening agent from Ciba-Geigy Corporation, Ardsley, N.Y.), The liquid compositions were used as pretreatments for exposed dentin surfaces in the order set forth hereinabove, while the resin composition is an example of a resinous adhesive according to the present invention.

EXAMPLE 19

Preparation of Filler Material

Filler material suitable for use in the dental restorative compositions of this invention was prepared as follows.

Borosilicate glass rods, available from Corning Glass Works, Corning, N.Y., were cut into cylindrical form. The resulting cylinders were loaded into a 5 gallon glass carboy until the carboy was half filled. The carboy was then filled with water, sealed and tumbled at 175 rpm for 168 hours to condition the glass rods.

The conditioned borosilicate glass rods were recovered and loaded into a 5 gallon polyvinylidene fluoride lined grinding vessel adapted for combined oscillatory and vibratory motion. The grinding vessel was loaded with the glass rods until three-quarters filled. Three kilograms of X-ray opaque barium borosilicate glass frit (ESSCHEM T-3000 available from Esschem Corporation, Essington, Pa.) having an average particle size diameter of 10 microns were added to the grinding vessel and then water was added to fill the grinding vessel. The vessel was then sealed and vibrated for 24 hours whereupon the barium borosilicate frit is ground to an average particle size diameter ranging between about 5 and 6 microns and sufficient borosilicate glass was abraded off the rods to provide a barium borosilicate/borosilicate glass mixture comprising about 89% barium borosilicate and about 11% borosilicate glass.

The resulting aqueous slurry was recovered and strained through a series of 200, 400 and 600 mesh screens. The resulting filtrate was subjected to vacuum filtration and then dried in a convection oven at 120° C. for 24 hours. The dried, milled filler was recovered and crushed and ground with a mortar and pestle to a fine powder.

Three kilograms of the dried, milled filler were charged to a glass carboy which was filled to one-half its volume with conditioned borosilicate glass rods prepared as described above. The carboy was then filled with six liters of a clear, colorless, aqueous solution of sodium hydroxide exhibiting a pH of 12 which was buffered with Na$_2$HPO$_4$. The loaded carboy was sealed and tumbled at 175 rpm for 4 hours. Thereafter, the resulting milled filler was recovered and subjected to vacuum filtration. The filter cake was washed with water until pH indicators in the filtrate indicated that neutrality (pH=5.5–7.0) had been essentially obtained. The recovered filter cake was then dried in a convection oven at 120° C. for 24 hours. The neutralized filter cake was ground to a fine powder with a mortar and pestle.

Silanization of the filler thus obtained was effected by filling a 5 gallon glass carboy to one-half its volume with borosilicate glass rods conditioned in the manner described hereinabove. Six kilograms of a solution of 8% silane in methanol was charged to the carboy along with 3 kilograms of the milled filler recovered from the aqueous etchant milling step. The carboy was sealed and tumbled for 6 hours at 175 rpm. The silanized slurry was recovered and subjected to vacuum filtration. The resulting filter cake was dried in a vacuum oven for one hour at 120° C. and then pulverized with mortar and pestle giving rise to silanized filler particles having an average particle size of 2.3 microns. Silanization results in 4.5% silane being coupled to the filler particles.

This filler material can be used with resin matrices containing polycarbonate dimethacrylates in either self-curing or visible light curing compositions.

EXAMPLE 20

Visible Light Curable Filled Dental Restorative Composition

A monomeric matrix composition was prepared by admixing the following ingredients:

100 grams of the monomeric matrix composition was prepared by admixing the following:
29.00 grams BIS-GMA
70.00 grams PCDMA (condensation product of 2-hydroxymethylmethacrylate and triethylene glycol bis(chloroformate)
0.99 gram TINUVIN P
0.16 grams dl-camphoroquinone
0.23 grams diethylamino ethylmethacrylate (DEAEMA)
0.0097 grams 2,2'-(2,5-thiophenediyl) bis(5-tert-butylbenzoxazole)

A filled composite restoration material of the present invention especially suitable for anterior dental applications was prepared by admixing 30% by weight of the foregoing monomeric matrix composition with 68% by weight of the inorganic filler of Example 19 and 2% by weight of colloidal fumed silica having an average particle size of about 0.04 micron. The resulting composite was a homogeneous paste comprising the monomeric composition as the matrix with the inorganic filler and the fumed silica uniformly dispersed therein.

EXAMPLE 21

Self-Curing Paste-Paste Dental Restorative Composition and Heat-Pressure Cure Restoration Composition An initiator resin system for a self cure resin, or single component system for a heat-pressure cure resin was prepared by admixing the following:
70.00 grams PCDMA
29.00 grams BIS-GMA
0.15 grams BHT
4.00 grams LUCIDOL benzoyl peroxide
0.0097 grams 2,2'-(2,5-thiophenediyl) bis(5-tert-butylbenzoxazole)

The initiator paste system was obtained by admixing 21% by weight of the above monomeric composition with 79% by weight of the inorganic filler of Example 19 in a planetary mixer under vacuum forming a homogeneous paste. The paste was passed through a two roll stainless steel mill to ensure homogeneity.

An accelerator resin for the self-cure system was prepared by admixing the following:
70.00 grams PCDMA
29.00 grams BIS-GMA
0.15 grams BHT
1.50 grams dihydroxyethyl p-toluidene (m.p.: 53.5°–54.5° C.)
4.00 grams UV-9 benzophenone The heat cure single paste dental restorative excludes the polymerization accelerator, i.e., the tertiary amines, such as dihydroxyethyl-para-toluidine or diethylaminoethylmethacrylate, and also excludes the visible light cure initiator d,l-camphoroquinone. Only the presence of the heat-cure initiator, benzoyl peroxide, is required in such a system.

The accelerator paste system was obtained by admixing 30% by weight of the above monomeric composition with 70% by weight of the inorganic filler of Example 19 in a planetary mixer under vacuum forming a homogeneous paste. The paste was passed through a two roll stainless steel mill to ensure homogeneity.

Essentially equal amounts of the foregoing initiator paste system and accelerator paste system were uniformly admixed for about one minute to form the dual-curing filled composite restorative material of the present invention.

EXAMPLE 22

This experiment was carried out to determine the bond strength of dentin adhesives. Three commercial dentin adhesives were tested in shear strength mode with the Universal Instron: (1) Scotchbond—3M Corp. (self-cure), which is a chlorophosphate ester of BIS-GMA diluted with triethylene glycol dimethacrylate; (2) Scotchbond—3M Corp. (visible light-cure), also a chlorophosphate ester of BIS-GMA diluted with triethylene glycol dimethacrylate; and (3) Pentra-Bond— Pentron Corp. (dual cure and self-cure), which is a combination of BIS-GMA with a polycarbonate dimethacrylate condensation product according to the present invention.

Specimen Preparation

Fifteen molar teeth preserved in 0.1% Thymol were mounted in 12 mm diameter plexiglass cylinders with cold-cure resin material. Approximately 1.5–2.0 nun of tooth-long axis was maintained in extruded fashion from cylinder. Using a slow speed dental saw, the coronal portion of the teeth were removed in lateral fashion so that the base of the pits and fissures remained intact. Then the pits and fissure floors were ground off with a silicon carbide strip/wheel (240 grit) and water to expose the dentin beneath the dentino-enamel-junction (DEJ).

The dentin surface was conditioned with 3% $H_2O_2$ for 1 minute, rinsed and dried for 45 seconds with a jet of oil free air (to remove superficial debris) and then treated with 5% NaOCl for 1 minute, rinsed and dried for 45 seconds (to remove the smear layer).

The manufacturer's instructions were followed for each group using dentin liquid and/or resin portions and the appropriate polymerization mode (self-cure; 3–5 minutes and visible light-cure; 40 seconds with Demetron-Optilux light). Five mounted and treated teeth were used for each group.

A Teflon split mold, guide, sleeve and screw assembly were placed on top of the adhesive coated tooth surface (Group I=Scotchbond self-cure; Group II=Scotchbond L.C.; Group III=Pentra-bond self-cure; Group IV=Pentra-bond dual-cure) and a 5 mm diameter cylinder of composite was built up using P-30, which is a visible light cure posterior composite filling material (3M Corp.) with Group I and II and Post-Com II L.C. visible light cure posterior composite filling material (Pentron Corp.) with Groups III and IV, in accordance with the manufacturer's instructions. The specimen mold assembly was left for 15 minutes undisturbed before removing the split mold and sleeve guide without exerting undue pressure. Specimens with flash of composite resin at the composite cylinder periphery were rejected in order to establish a uniform standard contact surface area. The specimens were then aged for 7 days at 37° C., 99.0% relative humidity and then tested for shear strength.

Testing

The Universal Instron machine was used with an adapted ADA fabricated bond-strength assembly for shear and tensile tests that accommodates the plexiglass cylinders with mounted molars (dentin adhesive bonded composite cylinders beneath DEJ). A knife edge disk surrounds the composite cylinder at the tooth-dentin-composite interface and a force with pull chain perpendicular to cylinder long axis is applied at 0.02 in/min cross head speed. The American Dental Association ADA fabricated apparatus avoids slippage and lateral movement inherent in Instron Universal joints and grips. The force was recorded and the diameter of composite cylinder measured with a digital pin-point micrometer (Mitutoyo) at the tooth/composite interface. The strength was calculated via $$\frac{F}{A} = \frac{\text{load (lbs)}}{\pi\, r^2\, (\text{in}^2)} = \text{psi}$$

The averages are noted below:

| | |
|---|---|
| Scotchbond/Self-cure P-30 | 300 psi |
| Scotchbond L.C./P-30 | 450 psi |
| Pentra-Bond/Self-cure Post Com II L.C. | 900 psi |
| Pentra-Bond dual cure/ Post-Com II L.C. | 1200 psi |

The Pentra-Bond/Post-Com II L.C. resin composition series shear strength/bond strength to dentin is significantly superior statistically (at $p<0.01$, 99.0% C.L. or greater) than the Scotchbond/P-30 3M Corp. series.

EXAMPLE 23

This experiment was also carried out to determine the bond strength of various commercially available adhesive resins to dentin. Eleven commercial dentin adhesives were tested in the shear strength mode with the Universal Instron:
(1) Scotchbond (self-cure)—3M Corp., which is a chlorophosphate ester of BIS-GMA diluted with triethylene glycol dimethacrylate;
(2) Scotchbond (visible light cure)—3M Corp., also a chlorophosphate ester of BIS-GMA diluted with triethylene glycol dimethacrylate;

(3) Scotchbond II (visible light cure)—3M Corp., which is a chlorophosphate ester of BIS-GMA diluted with triethylene glycol dimethacrylate and 2-hydroxyethylmethacrylate and includes on the polymeric chain backbone two carboxylic acid constituents tagged onto each monomer. The application of Scotchbond II is a two-step process:
 (a) a maleic acid layer is applied to remove the smear layer;
 (b) the bonding resin is applied and visible light cured.
(4) Gluma/Lumifor Columbus—Bayer Corp., which is a system comprising two topical applications followed by application of a conventional resin based upon BIS-GMA diluted with triethylene glycol dimethacrylate. The Gluma/Lumifor is applied as follows:
 (a) a 17% EDTA solution is applied to remove the dentin smear layer;
 (b) a 5% glutaraldehyde solution is applied in order to form a collagen graft (from dentin);
 (c) a 35% solution of 2-hydroxyethylmethacrylate is applied as a wetting agent; and
 (d) Lumifor bonding agent (visible light cure) is applied.
(5) Tenure/Visar Seal—Den-Mat Corp., which is a system comprising 3 topical applications followed by application of a conventional resin based upon BIS-GMA diluted with triethyleneglycoldimethacrylate. The Tenure/Visar Seal is applied as follows:
 (a) a solution comprising 2% nitric acid mixed with 6% iron oxalate or aluminum oxalate is applied to remove the smear layer to expose the dentin tubules, after which the tooth structure is rinsed with acetone and air-dried;
 (b) a solution of N-phenylglycine glycidylmethacrylate mixed with acetone and/or a powder comprising N-tolylglycine and/or N-phenyl glycine admixed with acetone is applied (10% glycine component to 90% acetone is applied) followed by an acetone rinse and/or drying;
 (c) PMDM, which is the reaction product of pyromellitic acid dianhydride with 2-hydroxyethyl methacrylate is applied followed by an acetone rinse and air drying; and
 (d) the BIS-GMA/TEGDMA bonding agent is applied.
(6) Creation/Visar Seal (visible light cure)—Den-Mat Corp., which is a resin comprising 98% ethylene glycol dimethacrylate. A solution of 6% citric acid is applied followed by topical application of the resin.
(7) Clearfil (self cure)-Kuraray Co., which is a resin comprising a diisocyanate/2-hydroxyethylmethacrylate component and an N-phenylglycine glycidylmethacrylate component admixed in a ratio of 1:1 prior to application.
(8) Bondlite (visible light cure)—Kerr/Sybron, which is a chlorophosphate ester of BIS-GMA diluted with triethylene glycol dimethacrylate.
(9) Restodent VL (visible light cure)—Lee Pharmaceuticals, which is an isocynate in methylene chloride;
(10) Dentin Adhesit/Heliobond (visible light cure)—Vivadent/Ivoclar, which is an isocyanate in methylene chloride. A 5% solution of sodium chloride is first applied to remove the smear layer.

(11) Pentra Bond II (visible light cure)—Jeneric/Pentron, which is a system in accordance with the present invention comprising two topical applications, followed by application of the PCDMA-based resin. The Pentra Bond II adhesive is prepared and applied in accordance with Example 18 herein.

Specimens were prepared in the same manner as in Example 22 herein, except that in each case the composite cylinder was built up using Pentra-Fil II (Jeneric/Pentron, Inc.), visible light cure anterior dental filling composite material. The manufacturer's instructions were followed for each group and the appropriate polymerization modes were employed. Five mounted and treated teeth were used for each group. All specimens were aged in distilled water at 37° C. and tested for shear strength at one hour, 24 hours and one week. The average results for the five specimens per group are set forth in Table I below:

TABLE I

| Product Name | Dentin Pull Shear Bond Strength (psi) | | | Without Smear Layer Removed |
|---|---|---|---|---|
| | 1 hour | 24 hours | 1 week | |
| Scotchbond S/C | 345 | 376 | 568 | — |
| | (116.86) | (94.56) | (177.14) | |
| Scotchbond VLC | 260 | 722 | 704 | — |
| | (5.38) | (135.14) | (133.54) | |
| Scotchbond II | 679 | 751 | 1030 | 200 |
| | (299.65) | (214.18) | ( ) | |
| Gluma/Lumifor | 281 | 412 | 596 | 150 |
| | (134.93) | (60.73) | ( ) | |
| Tenure/Visar Seal | 598 | 2107 | 1695 | 700 |
| | (298.41) | (385.05) | (180.07) | |
| Creation/ Visar Seal | 339 | 324 | 343 | — |
| | (117.63) | (206.14) | (187.20) | |
| Clearfil | 129 | 192 | 73 | — |
| | (52.31) | (272.00) | (106.18) | |
| Bondlite | 475 | 773 | 744 | — |
| | (193.63) | (191.87) | (181.10) | |
| Restodent VL | 16 | 114 | 98 | — |
| | (32.5) | (81.34) | (36.95) | |
| Dentin Adhesit/ Heliobond | 187 | 148 | — | |
| | (95.49) | (98.75) | | |
| Pentra-Bond II | 576 | 1042 | 1570 | 1540 |
| | (167.81) | (50.57) | (46.49) | (249.44) |

Selected products were additionally aged in distilled water at 37° C. for 47 days, and tested for shear strength. The average results for six specimens per group are set forth in Table 2 below.

TABLE II

| Product Name | Dentin Pull Shear Bond Strength 47 days | |
|---|---|---|
| | PSI | Standard Deviation |
| Scotchbond S/C | 325 | (135.68) |
| Scotchbond VLC | 425 | (211.96) |
| Tenure/Visar Seal | 1021 | (566.16) |
| Creation/ Visar Seal | 285 | (43.84) |
| Pentra-Bond II/ | 1540 | (60.91) |

The Pentra-Bond II adhesive shear bond strength to dentin and hydrolytic stability (long term aging) is significantly superior statistically (at $p<0.01$, 99.0% C.L. or greater) than the commercial materials both with and without removal of the smear layer. The Pentra-Bond II adhesive shear bond strength to dentin is statistically superior to the Tenure/Visar Seal System when the smear layer is not removed and in hydrolytic stability.

EXAMPLE 24

As known to those in the dental science, pull shear bond strength is not the only important property of dental adhesives. In addition, it is important that the dental adhesives themselves exhibit good resistance to impact, which can be measured by diametral tensile strength. If the dental adhesive itself is not sufficiently tough, it may microcraze or fracture even though the filling material does not prematurely fracture under application of stress/strain.

This experiment was carried out to determine the diametral tensile strengths and polymer shrinkages of commercial adhesives. The same commercial adhesives as described in Example 23 were tested in diametral tensile strength mode as well as for polymer shrinkage.

D.T.S.

The D.T.S. samples were prepared by preparing the various resins in accordance with the manufacturer's instructions and American Dental Association Specification No. 27, and subjecting the samples to the appropriate mode of cure. The eleven samples were cured in a 6 mm diameter×3 mm stainless steel split cylindrical molds, set on 25×75 mm glass microslides, and covered with a glass cover microslips, 25×25 mm. The cured samples were immersed within 2 minutes of curing into a 37° C.±0.1° C. distilled water bath for 15 minutes, retrieved and molds disassembled and stored in the 37° C.±0.1° C. distilled water bath for 24 hours. The samples were then subjected to a diametral tensile compression test on an Instron machine at 1 inch/minute chart speed and 0.2 inches/minute cross head speed and then the pounds of load applied/force to cause fracture of the specimens were noted and employed to calculate the D.T.S. (D.T.S.=2P/dl wherein P=load, d=specimen diameter and l=heigth of specimen; strength=force/surface area of specimen). The average of six specimen test results per system are summarized below.

Polymerization Shrinkage

Three 6×3 mm linear polymerization shrinkage (%) samples were prepared for each composition and subject to the appropriate mode of cure in accordance with the manufactures instructions. The % polymerization shrinkage was measured by the dimensional change which occurred after cure, 6 mesurements per specimen and 18 measurements per system. The results of the linear polymerization shrinkage testing are also set forth below.

| Product Name | D.T.S. 24 Hours (psi.) | Linear Polymerization Shrinkage (%) |
|---|---|---|
| Scotchbond S/C | 666 (24.32) | 3.73 (0.1916) |
| Scotchbond VLC | — | 3.70 (0.5869) |
| Scotchbond II | 5407 (149.60) | 1.53 (0.3064) |
| Gluma/Lumifor | 5421 (428.44) | 2.58 (0.8549) |
| Tenure/Visar Seal | 5227 (988.05) | 2.39 (.5048) |
| Creation/Visar Seal | 5227 (988.05) | 2.39 (.5048) |
| Bondlite | 1437 (254.88) | 2.00 (0.0450) |
| Dentin Adhesit/Heliobond | 4896 (267.06) | 1.18 (0.2359) |

-continued

| Product Name | D.T.S. 24 Hours (psi.) | Linear Polymerization Shrinkage (%) |
|---|---|---|
| Pentra-Bond II | 13,387 (174023) | 1.83 (0.1940) |

The results of the testing show Pentra-Bond II dental composition as being much tougher compared to other commercially available adhesives and in the lowest statistical subset of (%) linear polymerization shrinkage.

EXAMPLE 25

This experiment was carried out to determine the cytotoxicity of dentin adhesives. Eleven commercial dentin adhesives were tested by both the MEM Elution Cell Culture Extract Cytotoxicity Test and the Agar Diffusion Cell Culture Cytotoxicity Test. The commercial dentin adhesives tested are those described in Example 23 herein.

Four 6×1 mm samples were prepared for the Agar Difussion Test and three 6×1 mm samples were prepared for the MEM Elution test. Each sample was prepared in accordance with the manufactures instructions and subject to the appropriate mode of cure.

MEM Elution Cell Culture Cytotoxicity Test

After sample preparation as above, the samples were autoclaved for nine minutes at 121° C. in vials containing deionized water. Using all available sample, the specimen to solvent ratio for the extraction was 2.3 cm$^2$ surface area to one ml of Minimal Essential Medium (MEM). The samples were extracted for twenty four hours at 37° C. in MEM. One ml of the extract was then placed into a tissue culture dish containing a healthy monolayer of L-929 mouse fibroblast connective tissue cells, and the samples were then incubated again for 24 hours. After incubation the cultures were examined microscopically for confluency of the monolayer, crenation, vacuolization and cytolysis. A numerical rating for each of the four criteria was assigned as follows:

| Rating | Criteria |
|---|---|
| 0 | No evidence of cytoxicity |
| 1 | 1–25% of cells affected |
| 2 | 26–50% of cells affected |
| 3 | 51–75% of cells affected |
| 4 | 76–100% of cells affected |

A specimen is considered non-cytotoxic if all scores are 0.

A test is considered inconclusive if any score is greater than zero but no score is greater than 1.

A specimen is considered cytotoxic if a score of 2 or more is recorded in any category.

The results of the MEM Elution Cell Culture Testing are set forth in Table 1 below.

TABLE I

| Product Name | Confluency of Monolayer | Cre-nation | Vacuo-lation | Cyto-lysis |
|---|---|---|---|---|
| 1. Scotchbond S/C | 0 | 3 | 3 | 3 |
| 2. Scotchbond VLC | 0 | 1 | 1 | 1 |
| 3. Scotchbond II | 0 | 3 | 3 | 2 |
| 4. Ghuma/Lumifor | 0 | 3 | 3 | 2 |
| 5. Tenure/Visar Seal | 0 | 0 | 0 | 0 |

TABLE I-continued

| Product Name | Confluency of Monolayer | Cre-nation | Vacuo-lation | Cyto-lysis |
|---|---|---|---|---|
| 6. Creation/Visar Seal | 0 | 1 | 1 | 1 |
| 7. Clearfil | 0 | 0 | 0 | 0 |
| 8. Bondlite | 0 | 1 | 1 | 1 |
| 9. Restodent VL (liquid) | — | — | — | — |
| 10. Dentin Adhesit/ (liquid) Heliobond | — | — | — | — |
| 11. Pentra-Bond II | 0 | 0 | 0 | 0 |

Agar Diffusion Cytotoxicity Test

After sample preparation, the samples were autoclaved for nine minutes at 121° C. in vials containing dionized water. Two samples were then placed directly on the surface of agarose over a healthy monolayer of L929 cells and incubated for twenty-four hours. Positive and negative controls were run in accordance with ASTM F 895084 and A.D.A. Specification No. 41.

After incubation, the zone of toxicity was measured and the cells within the zone were microscopically inspected for confluency of the monolayer, crenation, vacuolization and cytolysis. The response index was expressed as follows: Response Index=Zone Index/Lysis Index.

The Zone Index and Lysis Index were determined as follows:

| | Description |
|---|---|
| Zone Index | |
| 0 | No detectable zone under or around specimen |
| 1 | Zone limited to area under specimen |
| 2 | Zone extends less than 0.5 cm beyond specimen |
| 3 | Zone extends 0.5 to 1.0 cm beyond specimen |
| 4 | Zone extends greater than 1.0 cm beyond specimen, but does not involve entire dish |
| 5 | Zone involves entire dish |
| Lysis Index | |
| 0 | No observable cytotoxicity |
| 1 | Less than 20% of zone affected |
| 2 | 20% to 39% of zone affected |
| 3 | 40% to 59% of zone affected |
| 4 | 60% to 80% of zone affected |
| 5 | Greater than 80% of zone affected |

A specimen is considered non-cytotoxic if all scores are 0. A test is considered inconclusive if no score is greater than 1. A specimen is considered cytotoxic if a score of 2 or more is recorded in any category. The results of the Agar Diffusion Test are set forth in Table II below.

TABLE II

| Product Name | Response Index | |
|---|---|---|
| 1. Scotchbond S/C | 1/3 | 1/3 |
| 2. Scotchbond VLC | 1/1 | 1/1 |
| 3. Scotchbond II | 1/4 | 1/4 |
| 4. Ghuma/Lumifor | 1/4 | 1/4 |
| 5. Tenure/Visar Seal | 0/0 | 0/0 |
| 6. Creation/Visar Seal | 1/1 | 1/1 |
| 7. Clearfil | 0/0 | 0/0 |
| 8. Bondlite | 1/2 | 1/2 |
| 9. Restodent VL (liquid) | 1/5 | 1/5 |
| 10. Dentin Adhesit/ (liquid) Heliobond | 1/4 | 1/4 |
| 11. Pentra-Bond II | 0/0 | 0/0 |

The adhesive prepared in accordance with the present invention (11) showed no cytotoxicity, which is an important property in addition to the other properties described herein.

EXAMPLE 26

The object of this experiment was to characterize the in-vitro wear performance of a series of experimental composites as a function of variable resin composition and curing method; visible light cured and heat/pressure cured small particle filled hybrid composites.

The filler composition was maintained constant including particulate morphology; size, shape and corresponding (distribution ranges) size=2.12 μm (0-5 μm), shape=1.30 aspect ratio, volume fraction =0.70 of a bariumborosilicate silanated filler and coupling agent content of 2.02%, (α-methacryloxypropyl-trimethoxysilane).

The resin matrix concentrations and purities of initiator, tertiary amine accelerator and inhibitor were maintained constant.

The base resin matrix composition was varied systematically in a series of three experimental pastes;
(A) BIS-GMA/triethylene glycol dimethacrylate (TEGDM);
(B) urethane dimethacrylate (UDMA)/TEGDM, both (A) and (B) visible light cure; and
(C) polycarbonate dimethacrylate/BIS-GMA, heat pressure cured while maintaining all other compositional parameters constant. The polycarbonate dimethacrylate employed was the condensation product of 2-hydroxyethylmethacrylate and triethyleneglycol bis(chloroformate).

It is necessary to heat pressure cure the PCDMA/BIS-GMA admix in proximity to its glass transition temperature such that semi-crystallinity will be induced. This is hypothesized to improve wear resistance.

On the other hand, if either BIS-GMA and/or PUDMA admixed with TEGDMA are heat pressure cured, this will naturally increase the degree of polymerization, but due to the amorphous structure of the above-noted polymers, semi-crystallinity will not be induced and hence wear resistance not significantly improved, although some nominal change may be noted.

Three (20×1 mm) discs of each composite based system were prepared by 5 quadrant illumination for 40 second exposure each in (A) and (B) to attain uniform cure (Optilux light—Demetron Corp.) and 8 minutes at 200° F. and 120 psi nitrogen gas pressure in a stainless steel heat/pressure vessel for system (C). The specimens were aged for one week at 37° C. water. The disc surfaces were occluded against sintered alumina pins which revolved at 29 rpm with 1 kg/mm$^2$ normal load for 48 hours each. The wear track grooves were then measured with a profilometer at 6 points per each of 3 wear-tracks produced for each paste system. The combined mean wear rates per system were then compared to the varied parameters; resin composition and curing methods. The statistical analysis of data inclusive of pearson correlation coefficient matrix of mean wear rates (μm/hr.) vs. varied parameters and a one-way Analysis of Variance (ANOVA) for wear readings across parameters variations revealed the following accordingly:

A. A statistically significant correlation exists between mean wear rates and curing method R=0.9, p<0.001 heat/pressure cure superior to visible light cure. Ranking respectively; (C)0.09 μm/hr.

(0.0121) (A)0.19 μm/hr. (0.0319) and (B)0.24 m/hr. (0.0041).

B. A statistically significant correlation exists between mean wear rates and resin matrix compositional variation R=0.9, p <0.001 ranking accordingly; (C) PCDMA/BIS-GMA <(A) BIS-GMA/TEGDM <(B) UDMA/TEGDM.

This superior wear resistance of admixed polycarbonate dimethacrylate/BIS-GMA particulate reinforced system coupled with heat-pressure cure compared to BIS-GMA or PUDMA visible light cured systems fits the theoretical assumptions that the degree of polymerization may be improved in curing a polymer above the glass transition temperature. This may be explained by polymer chain mobility in an inert environment under heat and pressure enabling semi-crystallization to occur producing a rigid, tough, porosity-free material with greater fatigue and wear resistance in comparison to the rigid and brittle characteristics typical of BIS-GMA or UDMA.

EXAMPLE 27

Method for Bonding a Dental Restorative Material to Dentin

The visible light curable dentin adhesive bonding system of Example 18 was employed herein. Two or three drops of the first component were applied to the exposed dentin and the solvent evaporated employing a jet of oil-free and moisture-free air. The second component was then applied by brushing it on the so prepared dental restoration. The second component was then thinned out to a thin film using a jet of oil-free and moisture-free air.

The thus coated dentin surface was then exposed to a visible light for 40 seconds to effect curing of the adhesive and the dental restorative material placed thereon.

EXAMPLE 28

Method for Bonding a Dental Restorative Material to Dentin

The self-curing dentin adhesive bonding system of Example 16 was employed herein. Two or three drops of the first component were applied to the exposed dentin and the solvent evaporated employing a jet of oil-free and moisture-free air. The second component was then applied by brushing it on the so prepared dental restoration. The second component was then thinned out to a thin film using a jet of oil-free and moisture-free air. The dental restorative material was then placed thereon.

EXAMPLE 29

This experiment was carried out to systematically characterize a series of dentin adhesives via sequential variations in three primary resin compositional constituents' concentrations, resin/diluent ratios, prepolymerization promoter, aromatic amino acid chelating agents, solvent choice, mode of cure, dentin smear layer and enamel and porcelain conditioning in order to optimize the bond strength properties of composite filling material to primarily dentin and, consequently, to enamel and porcelain.

The experimental design entailed the preparation of three resin materials ($R_1$, $R_2$ and $R_3$) having the constituents and mode of cure set forth below:

| Component | Amount (Parts) |
| --- | --- |
| Resin 1, Dual Cure ($R_1$) | |
| Polycarbonate dimethacrylate (PCDMA) | 50 |
| BIS—GMA | 20 |
| 2-hydroxyethylmethacrylate (2-HEMA) | 30 |
| Camphoroquinone | 0.1650 |
| Benzoyl peroxide (BPO) | 3.00 |
| BHT | 0.0746 |
| Benzotriazole (Tinuvin P) | 1.0000 |
| Resin 2, Visible Light Cure ($R_2$) | |
| PCDMA | 50 |
| BIS—GMA | 20 |
| 2-HEMA | 30 |
| Camphoroquinone | 0.1650 |
| Diethylaminoethylmethacrylate (DEA—EMA) | 0.2300 |
| BHT | 0.0146 |
| Benzotriazole | 1.0000 |
| Resin 3, Dual Cure, ($R_3$) | |
| PCDMA | 65 |
| BIS—GMA | 0 |
| 2-HEMA | 35 |
| Camphoroquinone | 0.1650 |
| BPO | 3.00 |
| BHT | 0.0746 |
| Benzotriazole | 1.0000 |

As can be seen, resins $R_1$ and $R_2$ are identical except that $R_1$ is dual cure, while $R_2$ is visible light curable. $R_3$ is a different dual cure resin.

In addition, liquid two-phase components ($L_1$–$L_4$) to be mixed and/or applied as preconditioners were prepared in various solvents; ethanol ($L_1$) and acetone ($L_2$, $L_3$ and $L_4$), principally to test the bond contribution in a visible light cured ($L_2$, $L_3$) and dual cure ($L_1$, $L_4$) modes. The influence of the application of a sodium benzene sulfinic acid prepolymer promoter ($L_2$), N-phenylglycine amino acid ($L_3$) and a 17% EDTA solution for smear layer removal were also tested. The liquid components were prepared by mixing together the following components in the stated proportions:

| Component | Amounts |
| --- | --- |
| Liquid 1, dual cure, ($L_1$) | |
| Ethanol | 96.0 |
| Sodium benzene sulfinic acid salt | 4.0 |
| DEAEMA 99% purity | 0.2300 |
| DHEPT 99% purity | 0.2500 |
| Liquid 2, visible light cure, ($L_2$) | |
| Acetone | 98.70 |
| Sodium benzene sulfinic acid salt | 1.30 |
| Liquid 3, visible light cure, ($L_3$) | |
| Acetone | 90.00 |
| N-phenylglycine, 98.0% purity | 10.00 |
| Liquid 4, dual cure, ($L_4$) | |
| Acetone | 96.0 |
| Sodium benzene sulfinic acid salt | 4.0 |
| DEAEMA 99% purity | 0.2300 |
| DHEPT 99.9% purity | 0.2500 |

The bond-strength test specimens (6 per group) were prepared by mounting freshly extracted molar teeth into plexiglass cylinders with cold-cure PMMA powder-liquid media with the coronal tooth portion projecting axially outward from the cylindrical mounts. The molar teeth were sectioned with a slow speed diamond wheel saw (South Bay Technologies, Temple City, Calif.) slightly beneath the dentino enamel junction exposing the tooth dentin surface and polished on 240 grit silicon carbide strips (Handimet II, Buehler Corp.

Lake Bluff, Ill.) in order to attain nominal surface roughness.

A sequential application of the experimental dental adhesive resins (R) and the liquid pretreatments (L) were applied onto the dentinal tooth surfaces, solvent evaporated from the liquid pretreatments employing a 5-10 second jet of oil-free, moisture-free air. Resins were then applied onto the liquid pretreated tooth surfaces, thinned to a uniform layer with a jet of oil-free, moisture-free air and either visible light cured for 40 seconds (Optilux, Demetron Corp., Danbury, Conn., or dual cured (visible light cured and self-cured simultaneously). The details of each experiment are given in Table I below.

TABLE I

| Group | Experimental Adhesives Series Applied to Dentin |
|---|---|
| I | $L_3, R_2$ |
| II | $L_3, R_3 + L_4$ |
| III | $L_3, R_3 + L_1$ |
| IV | $R_3 + L_4$ |
| V | $R_3 + L_1$ |
| VI | $L_3, R_1 + L_1$ |
| VII | $R_1 + L_1$ |
| VIII | $L_2, L_3, R_2$ |
| IX | $R_1 + L_4$ |
| X | $D_1, L_3, R_2$ |
| XI | EDTA, $L_2, L_3, R_2$ |

Thereafter, 5×5 mm cylindrical split stainless steel molds were placed on the liquid pretreated and/or resin coated dentin surfaces and secured with teflon sleeves. Cylinders of visible light cured hybrid small particle size filled composite (Pentra-Fil II, Jeneric/Pentron, Inc. Wallingford, Conn.) were built-up in the split molds, condensed and visible light cured for 40 seconds in 2 layers, 2.5 mm each. The test specimen assemblies were allowed to bench rest for 10 minutes in order to attain nominal polymerization, disassembled and placed in a water bath at 37° C. for 1 week and selectively for 24 hour aging periods.

The excess resin/composite paste flash was trimmed from the bond site perimeter with a high speed dental laboratory drill and green stones (Osada Co., Osada, Japan). The composite cylinder's bond site surface contact outer diameter at the tooth junction was measured with a digital micrometer (Mitutoyo Corp., Paramus, N.J.).

The samples were debonded on a Universal Instron (Canton, Ohio) at 0.02 in./min. cross head speed with an American Dental Association designed bond-strength test apparatus in order to determine the pull-shear bond-strength via a knife-edge disc straining the bond interface. The pull-shear bond strength was calculated ($P/r^2$ averages) and standard deviations computed. The results are set forth in Table II.

TABLE II

| Group | Average Pull-Shear Bond Strength to Dentin (psi) | Standard Deviation (psi) |
|---|---|---|
| I | 1144 | 99.41 |
| II | 520 | 70.07 |
| III | 1170 | 62.89 |
| IV | 21 | 6.36 |
| V | 707 | 88.17 |
| VI | 881 | 30.35 |
| VII | 141 | 19.92 |
| VIII | 1570 | 46.49 |
| IX | 131 | 0 |
| X | 161 | 0 |
| XI | 1540 | 249.44 |

Conclusions

A statistical analysis of variance of the variable experimental dentin adhesives series indicated: $F = 444.270$, $p < 0.001$. Therefore, a significant difference is apparent within the experimental adhesives composition and treatment modalities. Subsequently, a least significance difference procedure analysis accounting for standard deviation heterogeneity on raw and log transformed data of mean bond-strength values of the experimental adhesives series indicated in both instances the same subsets; VIII/X, III/I, VI, V, II, VII/IX and IV as significantly distinct subsets, $p < 0.001$.

The effect of changing the solvent from ethanol to acetone when the resin matrix is dual cure with resin: diluent ratio (1) ($R_1$) can be determined by comparing the shear bond results of Group VII with Group IX, wherein the only difference in the materials applied is the solvent component. A nonsignificant difference is seen between Group VII, 141 psi. and Group IX, 131 psi.

A different result is reached when the dual cure resin has resin: diluent (2) ($R_3$). When Group IV is compared with Group V, wherein again the only difference in the materials applied is the nature of the solvent, a significant difference in bond strength is apparent, 707(V) vs. 21 (IV), illustrating a preference for ethanol as the solvent/bond interaction media for the dual cure sodium salt prepolymerization promoter.

The effect of N-phenylglycine pretreatment on the dual cure resin of resin: diluent ratio (1) ($R_1$) admixed with the dual cure liquid using ethanol as the solvent ($L_1$) can be estimated by comparing the shear bond results from Group VI with those from Group VIII. The addition of the pretreatment step using N-phenylglycine in acetone ($L_3$) in Group VI exhibits a significant improvement in bond strength; an increase from 141 (VII) to 881 (VI) psi.

A statistically significant, although less dramatic, improvement in bond strength is again seen when an N-phenylglycine pretreatment is employed with a dual cure resin, resin: diluent ratio (2) ($R_3$) admixed with dual cure liquid including acetone as the solvent. This difference is seen by comparing the shear bond results of Group IV with Group II, 21 psi. v. 520 psi., wherein N-phenylglycine pretreatment is employed in Group II.

A particularly significant increase in bond strength is obtained when an N-phenyglycine pretreatment step is employed with the dual cure resin, resin/diluent ratio (2), $R_3$ and ethanol solvent for the dual cure prepolymerization promoter. This difference is demonstrated by comparing the shear bond strength results from Group I with Group III, 707 psi. v. 1170 psi., respectively, wherein the N-phenylglycine in acetone solution is applied in the Group III materials.

A comparison of the average shear bond strength of Group I, visible light cure resin $R_2$ with a pretreatment step of N-phenylglycine in acetone, with those of Group III, the dual cure counterpart also including the N-phenylglycine pretreatment step illustrates that there is no particular preference for the dual cure of the self cure resin. A nonsignificant difference is apparent between Group I (1144 psi.) and Group III (1170 psi.).

When the N-phenylglycine pretreatment/visible light cure resin (Group I) is augmented with a separate primary pretreatment solution (VIII), a significant increase in bond strength is apparent, 1144 to 1570 psi., correspondingly.

In the event that the dentin smear layer is removed, and thereafter a prepolymerization solution of a sulfinate sodium salt is applied, followed by treatment with N-phenylglycine in acetone and then the visible light cure resin is applied to dentin (XI) 1540 psi., a nonsignificant difference in bond strength is observed in comparison with Group VIII (1570 psi.) which comprises the identical application, except that the smear layer remains intact.

EXAMPLE 30

This example demonstrates the superiority of the dentin adhesive of the present invention when compared to one of the closest known materials in the prior art.

Sutagina, et al, U.S.S.R. Patent No. SU(11)1,113,1-12A (September 15, 1984) discloses a composite for undercoating metallic prostheses. The adhesive resin formula of Sutagina comprises:

| Material | % (wt) |
| --- | --- |
| Methylmethacrylate-methylacrylate copolymer | 11.0–12.0 |
| Triethylene glycol dimethacrylate | 25.0–29.0 |
| Oligocarbonate methacrylate | 8.5–11.5 |
| Epoxy-resin-methacrylic acid adduct | 25.0–30.0 |
| Diphenylolpropane dimethacrylate | 2.5–3.5 |
| Benzoyl peroxide | .4–.6 |
| Titanium dioxide | Remainder |

The system disclosed in Sutagina et al requires a powder to liquid system mixed at a 2:1 ratio, wherein the powder is composed of methylmethacrylate benzoyl peroxide and titanium dioxide and the liquid component contains the remainder of the ingredients. Sutagina teaches that the metallic dental prostheses are coated with the thus prepared formulation and bonded to a plastic/acrylic type facing/onlay and dry cured at 110° C. for 5 minutes.

In order to formulate an equivalent dentin adhesive resin based upon Sutagina et al for bonding intraorally (37° C.), the benzoyl peroxide free radical chain polymerization auto-cure peroxide initiator and heat (110° C.) initiating and propagating polymerization/cure process were substituted with optimum amounts/concentrations/purity of camphoroquinone (2,3-d-bornandione), a visible light cure initiator, and diethylaminoethylmethacrylate, a liquid tertiary amine polymerization accelerator as per the adhesive formulae of the present invention clinical indication and mode of cure. The titanium dioxide whitening/filler agent was omitted since otherwise it would interfere with light permeation and hinder the depth of cure capability. A dentin-/universal-simulated equivalent Sutagina visible light cure resin was thus prepared:

| Materials | Manufacturer | City/State | (Part) Amount |
| --- | --- | --- | --- |
| Methylmethacrylate | Esschem Co. | Essington, PA | 11.5 |
| Triethyleneglycol-dimethacrylate | Esschem Co. | Essington, PA | 26.8 |

-continued

| Materials | Manufacturer | City/State | (Part) Amount |
| --- | --- | --- | --- |
| Epoxy resin methacrylic acid adduct (Bis-phenol-A-diglycidylmethacrylate) | Freeman Corp. | Port Wash., WI | 27.1 |
| Oligocarbonate methacrylate (polycarbonate dimethacrylate 99.9% purity, M.W. = 462) | Jeneric/Pentron | Wallingford, CT | 10.0 |
| Diphenylolpropan-edimethacrylate | Esschem Co. | Essington, PA | 3.0 |
| d,l-camphoroquinone (99.0% purity) | Aldrich Co. | Milwaukee, WI | 0.1650 |
| diethylaminoethyl-methacrylate (98.5% purity) | CPS Corp. | Old Bridge, NJ | 0.2300 |

It should be noted that the methylmethacrylate utilized in Sutagina's formulae is not ideal for intra-oral cure type monomeric adhesive, since methylmethacrylate is a low molecular weight, cytotoxic and unbiocompatible material which is known not to achieve sufficient amount of carbon, carbon double bond conversion and hence a significant amount of residual monomer post-cure. One of the options to overcome this phenomenon is high temperature acceleration of conversion as noted per Sutagina's process, although not possible in the clinical intra-oral cure bonding case. The residual methylmethacrylate leads to gingival (gum tissue) inflamation, mucous membrane and tooth pulp irritation due to its cytoxic properties. However, for the purpose of the present comparative situation, the methylmethacrylate component was incorporated into the visible light cure equivalent adhesive formula.

The methylmethacrylate, triethylene glycol dimethacrylate, polycarbonate dimethacrylate and diphenylolpropanedimethacrylate were mixed until a homogenous dispersion was obtained. The camphoroquinone was then added while mixing until it was uniformly dispersed, after which the diethylaminoethylmethacrylate was added and dispersed by mixing. The BIS-GMA was added last, while mixing until the BIS-GMA was thoroughly dissolved and dispersed homogenously.

The pull shear bond strength of Pentral Fil II visible light cure anterior dental filling composite material (Jeneric/Pentron, Wallingford, Conn.), bonded to dentin, enamel, porcelain and non-precious metallic alloy using the Sutagina equivalent adhesive resin, was then determined as was the pull shear bond strength of Pentra Fil II bonded to the same substrates using an adhesive of the present invention, prepared in accordance with Example 18 herein.

Specimen Preparation

The following substrates were employed in this comparative study.

1. Intact dentin, freshly extracted teeth, 240 grit surface roughness.
2. Etched enamel, freshly extracted teeth (37% O—$H_3PO_4$ etched, rinsed dry).
3. Optec high strength dental procelain (Jeneric/Pentron, Inc., Wallingford, Conn.); sandblasted (5 sec., 50 min. $Al_2O_3$).
4. Optec high strength dental porcelain; etched (Chameleon Supertech porcelain etchant, hydroflouric acid based, Myrons Dental, Kansas City, Kans.).

5. Rexillium III non-precious Ni—Cr—Be dental alloy (Jeneric/Pentron, Inc.); sandblasted (5 sec., 50 min., Al$_2$O$_3$).

The substrates were prepared in accordance with techniques well known in the art, mounted in 12 mm diameter plexiglass cylinders with cold cure polymethylmethacrylate resin mounting material and further prepared for pull shear bond strength testing.

The Sutagina equivalent resin or dental adhesive of Example 18 of the present invention was then applied to the prepared substrate surface on a thin layer and visible light cured for 40 seconds per layer using an Optilux light source (Demetron Corp., Danbury, Conn.). Six mounted and treated specimens were used for each group.

A Teflon split mold, guide, sleeve and screw assembly were placed on top of the adhesive coated surfaces and a 5 mm diameter cylinder of Pentra Fil II visible light cure anterior dental filling composite material was built up. The specimen mold assembly was left undisturbed for 15 minutes before removing the split mold and sleeve guide.

Specimens with flash of composite resin at the composite cylinder periphery were rejected in order to establish a uniform standard contact surface area. The specimens were then aged for one week at 37° C. and then tested for shear strength.

Testing

The specimens were debonded on a Universal Instron Machine (Instron Co., Canton, Ohio) at about 0.02 inches per minute cross head speed in a tensile motion with a knife edge disc exerting a pull shear force at the bonded interface. The results of the pull shear bond strength testing is set forth below.

SUMMARY OF RESULTS

|  | Substrates | | | | |
|---|---|---|---|---|---|
|  | 1 Dentin | 2 Etched Enamel | 3 Sandblasted Porcelain | 4 Etched Porcelain | 5 Sandblasted Metallic Alloy |
| SUTAGINA | | | | | |
| Adhesive Bond-strength, psi, and (S.D.) | 16.8 (41.23) | 1,085 (244.68) | 598 (91.98) | 2,020 (502.12) | 1,134 (204.33) |
| EXAMPLE 18 | | | | | |
| Adhesive Bond-strength, psi, and (S.D.) | 1,570 (46.49) | 3,492 (173.77) | 2,440 (172.35) | 2,503 (71.02) | 1,933 (281.52) |

A one way analysis of variances and t-tests demonstrate a most significant difference between the Sutagina equivalent and the universal dental adhesive of the present invention with respect to bond strength within each category or substrate bonded. Within a confidence level of 99.99% or better, it can be concluded that the adhesive of the present invention generates a statistically superior bond-strength to all clinical indication intra-oral dental bonded substrates.

What is claimed is:

1. A dental resin composition which comprises:
   (A) from about 30 to about 80 weight percent of a polycarbonate dimethacrylate of the formula:

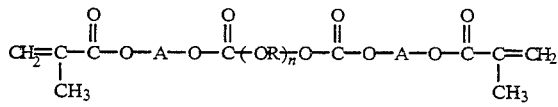

wherein A is $C_1$–$C_6$ alkylene, R is $C_2$–$C_6$ alkylene, R is $C_2$–$C_5$ alkylene having at least 2 carbon atoms in its principal chain and n is an integer from 1 to 4;
   (b) from about 5 to about 60 weight percent of a secondary monomer suitable for dental applications for imparting strength and rigidity to said dental resin composition, said secondary monomer being urethane dimethacrylate; and
   (c) from about 0 to about 50 weight percent of a diluent monomer for decreasing the viscosity of said dental resin composition,
   wherein each of the components (A), (B), and (C) is a different monomer and such that the specific amounts within the ranges yield a 100% by weight polymerization system.

2. A dental restorative composition which comprises:
   1. A dental resin composition according to claim 1; and
   2. An inorganic filler.

3. A dental restorative composition according to claim 2, wherein the diluent monomer of the resinous component is selected from the group consisting of 2-hydroxyethylmethacrylate, 2-hydroxypropylmethacrylate, ethylene glycol dimethacrylate, diethylene glycol dimethacrylate, triethylene glycol dimethacrylate, tetraethylene glycol dimethacrylate, 1,6-hexamethylene diisocyanate and 1,6-hexanedioldimethacrylate.

4. A dental restorative composition according to claim 3, wherein said secondary monomer is urethane dimethacrylate and said diluent monomer is 2-hydroxyethylmethacrylate.

5. A dental restorative composition according to claim 2, wherein the inorganic filler is selected from the group consisting of silica, silicate glass, quartz, barium borosilicate, strontium silicate, barium silicate, strontium borosilicate, borosilicate, lithium silicate, amorphous silica, calcium phosphate, alumina, zirconia, tin oxide and titania.

6. A dental restorative composition according to claim 5 for use as a dental crown and bridge material comprising from about 20 to about 40 weight percent of the resinous component and from about 60 to about 80 weight percent of the inorganic filler.

7. A dental restorative composition according to claim 5 for use as a luting cement which comprises from about 27 to about 70 weight percent of the resin component and from about 30 to about 73 weight percent of the inorganic filler.

8. A dental restorative composition according to claim 5 for use as an orthodontic sealant or cement which comprises from about 90 to about 100 weight percent of the resinous component and from about 0 to about 10 weight percent of inorganic filler.

9. A dental resin composition according to claim 1, wherein said diluent monomer is selected from the group consisting of 2-hydroxyethylmethacrylate, 2-hydroxypropylmethacrylate, ethylene glycol dimethacrylate, diethylene glycol dimethacrylate, triethylene glycol dimethacrylate, tetraethylene glycol dimethacrylate; 1,6-hexamethylene diisocyanate and 1,6-hexanedioldimethacrylate.

10. A dental resin composition according to claim 9, wherein said secondary monomer is urethane dimethacrylate and said diluent monomer is 2-hydroxyethylmethacrylate.

11. A dental resin composition according to claim 10, wherein the polycarbonate dimethacrylate is present in an amount of about 40 to about 72 weight percent, the urethane dimethacrylate is present in an amount of about 15 to about 35 weight percent, and the 2-hydroxyethylmethacrylate is present in an amount of about 20 to 40 weight percent, such that the specific amounts within the ranges yield a 100% by weight polymerization, said composition further comprising from about 0.05 to about 0.5 weight percent dl-camphoroquinone as a polymerization initiator, from about 0.05 to about 0.5 weight percent of diethylamino ethylmethacrylate as a polymerization accelerator, and from about 0.05 to about 5 weight percent of 2-(2-hydroxy-5 methylphenyl)-benzotriazole or benzophenone as an ultraviolet absorber.

12. A dental resin composition according to claim 10, wherein the polycarbonate dimethacrylate is present in an amount of about 40 to about 72 weight percent, the urethane dimethacrylate is present in an amount of about 15 to about 35 weight percent, and the 2-hydroxyethylmethacrylate is present in an amount of about 20 to 40 weight percent, such that the specific amounts within the ranges yield a 100% by weight polymerization, said composition further comprising from about 2 to about 6 weight percent of benzoyl peroxide as a polymerization initiator, from about 0.05 to about 4.0 weight percent dihydroxyethyl-p-toluidine as a polymerization accelerator and from about 0.05 to about 5.0 weight percent of 2-(2'-hydroxy-5'-methyphenyl)-benzotriazole or a benzophenone as an ultraviolet absorber.

13. A dental resin composition according to claim 10, wherein the molecular weight of said polycarbonate dimethacrylate ranges from about 400 to about 550.

14. A dental resin composition according to claim 10, in which, in the polycarbonate dimethacrylate, A is a $C_2$ or $C_3$ alkylene, R is ethylene or propylene, and n is 2 or 3.

15. A dental resin composition according to claim 14, in which the polycarbonate dimethacrylate is the condensation product of 2-hydroxyethylmethacrylate and triethylene glycol bis(chloroformate).

16. A dental resin composition according to claim 15, wherein the polycarbonate dimethacrylate is present in an amount of about 70 weight percent, the urethane dimethacrylate is present in an amount of about 30 weight percent, and the 2-hydroxyethylmethacrylate is present in an amount of about 0 weight percent.

17. A dental resin composition according to claim 15, wherein the polycarbonate dimethacrylate is present in an amount of about 40 to about 72 weight percent, the urethane dimethacrylate is present in amount of about 15 to about 35 weight percent, and the 2-hydroxyethylmethacrylate is present in an amount of about 20 to about 40 weight percent, such that the specific amounts within the ranges yield a 100% by weight polymerization system.

18. A dental resin composition according to claim 17, wherein the polycarbonate dimethacrylate is present in an amount of about 50 weight percent, the urethane dimethacrylate is present in an amount of about 20 weight percent, and the 2-hydroxyethylmethacrylate is present in an amount of about 30 weight percent.

19. A dental resin composition which comprises: urethane dimethacrylate in an amount ranging from about 20 to about 60 weight percent and a polycarbonate dimethacrylate of the formula

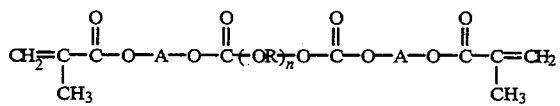

wherein A is $C_1$–$C_6$ alkylene, R is $C_2$–$C_5$ alkylene having at least 2 carbon atoms in its principal chain and n is an integer from 1 to 4, said polycarbonate dimethacrylate being present in an amount ranging from about 40 to about 80 weight percent.

20. A dental resin composition comprising from about 30 to about 80 weight percent of a polycarbonate dimethacrylate of the formula:

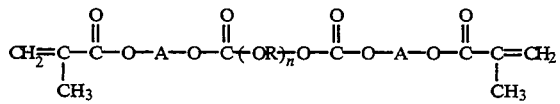

wherein A is $C_1$–$C_6$ alkylene, R is $C_2$–$C_5$ alkylene having at least 2 carbon atoms in its principal chain and n is an integer from 1 to 4; from about 5 to about 40 weight percent of urethane dimethacrylate; from about 10 to about 50 of 2-hydroxyethylmethacrylate.

* * * * *